US010058473B2

(12) United States Patent
Oshima et al.

(10) Patent No.: US 10,058,473 B2
(45) Date of Patent: Aug. 28, 2018

(54) TRAINING APPARATUS

(71) Applicants: Murata Machinery, Ltd., Kyoto-shi, Kyoto (JP); Teijin Pharma Limited, Chiyoda-ku, Tokyo (JP)

(72) Inventors: Osamu Oshima, Kyoto (JP); Yuichiro Minato, Kyoto (JP); Akihiro Maeda, Chiyoda-ku (JP); Fumi Fujita, Chiyoda-ku (JP); Jun Takeda, Chiyoda-ku (JP)

(73) Assignees: Murata Machinery, Ltd. (JP); Teijin Pharma Limited (JP)

( * ) Notice: Subject to any disclaimer, the term of this patent is extended or adjusted under 35 U.S.C. 154(b) by 41 days.

(21) Appl. No.: 15/036,547

(22) PCT Filed: Nov. 12, 2014

(86) PCT No.: PCT/JP2014/079952
§ 371 (c)(1),
(2) Date: May 13, 2016

(87) PCT Pub. No.: WO2015/071480
PCT Pub. Date: May 21, 2015

(65) Prior Publication Data
US 2016/0296405 A1 Oct. 13, 2016

(30) Foreign Application Priority Data
Nov. 14, 2013 (JP) .................... 2013-235827

(51) Int. Cl.
*A61H 1/02* (2006.01)
*A61B 5/11* (2006.01)
(Continued)

(52) U.S. Cl.
CPC .......... *A61H 1/0237* (2013.01); *A61B 5/1122* (2013.01); *A61B 5/1124* (2013.01);
(Continued)

(58) Field of Classification Search
CPC .... A61H 1/02–1/0214; A61H 1/0237–1/0288; A63B 21/0058; A63B 23/1281; A63B 24/00
See application file for complete search history.

(56) References Cited

U.S. PATENT DOCUMENTS 5,211,161 A * 5/1993 Stef ...................... A61H 1/0266
601/31
9,554,966 B2 * 1/2017 Kuro .................... A61H 1/0274
(Continued)

FOREIGN PATENT DOCUMENTS

| JP | 2005-118466 A | 5/2005 |
| JP | 2005-348779 A | 12/2005 |
| WO | 2012-117488 A1 | 9/2012 |

OTHER PUBLICATIONS

English language translation of International Search Report dated Feb. 17, 2015 issued in corresponding PCT application PCT/JP2014/079952.
(Continued)

*Primary Examiner* — Valerie L Woodward
(74) *Attorney, Agent, or Firm* — DLA Piper LLP (US)

(57) ABSTRACT

A training apparatus includes a fixed frame, an training rod, a motor, a rotation information detection sensor, a tilt angle calculation unit, a feedback current detection unit, a position difference calculation unit, and a determination unit. The training rod tilts with at least one degree of freedom. The motor tilts the training rod. The rotation information detection sensor outputs an amount of rotation of the motor. The tilt angle calculation unit calculates a tilt angle. The feedback current detection unit detects a feedback current value. The position difference calculation unit calculates a position difference every time when a first time period elapses. The determination unit determines an error when the position difference generated during the first time period is a first
(Continued)

threshold or higher, or when the feedback current value keeps a first current value or higher for a second time period or longer.

14 Claims, 21 Drawing Sheets

(51) Int. Cl.
*A63B 21/00* (2006.01)
*A63B 23/12* (2006.01)
*A63B 24/00* (2006.01)
*A63B 21/005* (2006.01)
*A63B 23/035* (2006.01)
*G06F 19/00* (2018.01)
*A63B 71/06* (2006.01)

(52) U.S. Cl.
CPC ....... *A61H 1/0274* (2013.01); *A63B 21/0058* (2013.01); *A63B 21/00072* (2013.01); *A63B 21/00178* (2013.01); *A63B 21/4017* (2015.10); *A63B 21/4033* (2015.10); *A63B 21/4035* (2015.10); *A63B 21/4047* (2015.10); *A63B 23/03508* (2013.01); *A63B 23/1281* (2013.01); *A63B 24/0006* (2013.01); *A63B 24/0062* (2013.01); *A63B 24/0087* (2013.01); *G06F 19/3481* (2013.01); *A61B 2505/09* (2013.01); *A61H 2201/1207* (2013.01); *A61H 2201/1215* (2013.01); *A61H 2201/1659* (2013.01); *A61H 2201/5035* (2013.01); *A61H 2201/5038* (2013.01); *A61H 2201/5043* (2013.01); *A61H 2201/5046* (2013.01); *A61H 2201/5048* (2013.01); *A61H 2201/5061* (2013.01); *A61H 2201/5064* (2013.01); *A61H 2201/5069* (2013.01); *A61H 2201/5084* (2013.01); *A63B 23/0355* (2013.01); *A63B 71/0622* (2013.01); *A63B 2024/0071* (2013.01); *A63B 2024/0093* (2013.01); *A63B 2208/0247* (2013.01); *A63B 2220/13* (2013.01); *A63B 2220/20* (2013.01); *A63B 2220/30* (2013.01); *A63B 2220/31* (2013.01); *A63B 2220/34* (2013.01); *A63B 2220/40* (2013.01); *A63B 2220/51* (2013.01); *A63B 2230/436* (2013.01)

(56) References Cited

U.S. PATENT DOCUMENTS

2006/0293617 A1* 12/2006 Einav .................. A61H 1/0274
                                                                            601/33
2009/0227911 A1*  9/2009 Srivastava ............. A61H 1/024
                                                                            601/34

OTHER PUBLICATIONS

International Preliminary Report on Patentability dated May 17, 2016, issued on corresponding International application No. PCT/JP2014/079952.

* cited by examiner

TRAINING APPARATUS

CROSS REFERENCE TO RELATED APPLICATIONS

This application is a national stage of international application no. PCT/JP2014/079952, filed on Nov. 12, 2014, and claims the benefit of priority under 35 USC 119 of Japanese application no. 2013-235827, filed on Nov. 14, 2013, both of which are incorporated herein by reference in their entirety.

TECHNICAL FIELD

The present invention relates to a training apparatus equipped with a training rod driven by a motor, for supporting rehabilitation of upper and/or lower limbs of a patient according to a predetermined training program.

BACKGROUND ART

Rehabilitation aimed at motor function recovery of upper and/or lower limbs of a stroke patient with hemiplegia is usually performed by an occupational therapist or a physical therapist, and hence there is a limitation in efficient offering of rehabilitation. For instance, in rehabilitation aimed at motor function recovery of an upper limb, it is mainly required to repeat as much as possible a correct movement of the paralyzed upper limb passively and actively in a movement range slightly larger than current range. On the basis of the rehabilitation for the motor function recovery, the occupational therapist or the physical therapist teaches the correct movement to the patient and manually applies a load on the upper limb of the patient so as to induce an active movement.

In this rehabilitation, the number of repetitions is limited due to exhaustion of the therapist. In addition, there may be a difference of medical quality of the rehabilitation depending on experience of the therapist. Accordingly, in order to support the training by the therapist, to eliminate the limitation due to exhaustion, and to standardize the medical quality as much as possible, there is known a training apparatus as described in Patent Citation 1, for example, which supports rehabilitation of a patient with a disabled limb such as an arm. The apparatus is disclosed as an upper limb training apparatus including a fixed frame that can be placed on a floor, a movable frame supported by the fixed frame so as to be capable of tilting in all directions, and a training rod attached to the movable frame in an expandable/contractible manner so as to be operated by a person who undergoes the training.

PRIOR ART CITATIONS

Patent Citation

Patent Citation 1: PCT publication No. 2012/117488

SUMMARY OF INVENTION

Technical Problem

The training apparatus as disclosed in Patent Citation 1, mainly in a case where a person who undergoes a training trains a limb, for example, an upper limb in accordance with a training program, monitors whether or not the movement of the upper limb to be trained is following the movement of the training rod, and teaches the movement of the training rod to the user of the training apparatus, as necessary, on the basis of visual or auditory information. In this case, the conventional training apparatus evaluates whether or not the movement of the upper limb to be trained is following the movement of the training rod instructed by the training program, by a calculation operation inside the apparatus, for example, on the basis of only a level of difference (a position difference) between an angle to tilt the training rod instructed by the training program and an actual tilt angle of the training rod. However, by only this evaluation method based on a level of position difference, a rapid position difference generated in a short period cannot be distinguished from a slowly and gradually changing position difference. In addition, because the conventional training apparatus cannot distinguish the two types of position differences described above, the user of the apparatus cannot determine which factor causes the position difference. Accordingly, the user of the conventional training apparatus may not undergo appropriate training program.

In addition, the training apparatus is required to have a function of monitoring the position difference as well as a load amount necessary for the training rod to move the upper limb, in order to appropriately grasp a load on the patient during the training and to feedback the load to the training. However, because the level of the position difference is the difference between the instructed angle to tilt and the actual tilt angle, it is difficult to correctly monitor the load amount on the basis of only a measured value thereof, and hence it is necessary to monitor on the basis of another indicator.

It is an object of the present invention to provide a training apparatus for rehabilitation support, which correctly monitors a temporal change difference of position difference and a load amount necessary for the training rod to move the limb to be trained at the same time, so as to appropriately control the training rod.

Technical Solution

As means for solving the problem, a plurality of embodiments are described below. These embodiments can be arbitrarily combined as necessary.

A training apparatus according to an aspect of the present invention is a training apparatus for training upper and/or lower limbs of a user in accordance with a predetermined training program. The training apparatus includes a fixed frame, a training rod, a motor, a rotation information detection sensor, a tilt angle calculation unit, a feedback current detection unit, a position difference calculation unit, and a determination unit. The fixed frame is placed on or in the vicinity of a floor. The training rod is supported by the fixed frame in a manner capable of tilting about a predetermined tilting axis with at least one degree of freedom. Further, the training rod holds a limb. The motor tilts the training rod about the tilting axis. The rotation information detection sensor outputs an amount of rotation of the motor. The tilt angle calculation unit calculates a tilt angle of the training rod on the basis of the amount of rotation of the motor. The feedback current detection unit detects a feedback current of the motor. The position difference calculation unit calculates a position difference every time when a predetermined first time period elapses. Here, the position difference is a difference between an actual tilt angle of the training rod and an instructed tilt angle of the training rod instructed by the training program. The determination unit determines an error when the position difference during the first time period is a predetermined first threshold or higher, or when the feedback current is kept a first current or higher for a predetermined second time period or longer.

In this training apparatus, when the motor controls the training rod, the position difference calculation unit calculates the position difference every first time period. Further, when the position difference during the first time period becomes the first threshold or higher, the determination unit determines that a malfunction has occurred in the training apparatus or that the position difference has rapidly changed in a short period, so as to detect an error.

On the other hand, when the motor controls the training rod, the feedback current detection unit monitors the feedback current supplied to the motor. Further, when feedback current is kept the first current or higher for the second time period or longer, so as to detect an error, the determination unit determines that a malfunction has occurred in the training apparatus or that a slow position difference change has continued for long period.

In this way, this training apparatus monitors a position difference change per the first time period. Accordingly, the determination unit can determine a position difference that has rapidly changed in a short period with reference to the first time period, if the position difference change in the first time period is large. Then, the determination unit can detect an error when the rapid position difference change has occurred.

In addition, the training apparatus monitors the feedback current input to the motor, and hence can monitor a torque necessary for the motor to tilt the training rod.

Further, the training apparatus controls the training rod at the tilt angle instructed by the training program, and hence the feedback current changes in accordance with a level of the position difference change. Accordingly, on the basis of the feedback current value and the predetermined determination time period, it is possible to monitor whether a slow position difference change is generated or a rapid position difference change is generated.

In addition, when the feedback current is kept the first current value or higher for the second time period or longer, the determination unit determines that an error has occurred. In this way, if the position difference is within a constant range in the determination time period, i.e., if the motor (the training rod) does not apply an excessive load on the limb of the patient, or if the position difference is slowly changed (if the limb of the patient is following the movement of the training rod to a certain extent so that the training can be continued), it is possible to control the training apparatus to continue the training until the second time period elapses.

The training rod may expand and contract in a longitudinal axis direction. Here, the longitudinal axis direction means a longitudinal direction of the training rod. If the training rod is capable of expanding and contracting in the longitudinal axis direction, it is possible to carry out training of an upper limb or a lower limb in the longitudinal direction of the training rod.

The training apparatus may further include an information providing unit. The information providing unit provides the users including a patient, a training aid and a health care worker with visual or auditory information when the determination unit determines an error.

In this way, it is possible to notify the patient and the user of the training apparatus about a status of the training apparatus, i.e., that an error has occurred in the training apparatus, and/or about a cause of the error.

The information providing unit may provide the user with information when the user has moved the training rod to reach a preset passing point in a training route set by the training program. In this way, the user can know that the training rod has been moved just in accordance with the training program. In addition, because the user is provided with the visual or auditory information when the user has moved the training rod to reach the preset passing point, the patient can maintain a motivation to continue the training.

When an error is determined by the determination unit, rotation of the motor may be stopped. In this way, when an error has occurred, the training apparatus can be surely stopped.

The training apparatus may further include a feedback current limiting unit. The feedback current limiting unit limits the feedback current of the motor to an appropriately preset second current value when the determination unit determines an error.

In this way, when an error has occurred in the training apparatus, an output torque of the motor can be limited. As a result, the training rod can be controlled so as to carry out the rehabilitation without applying an excessive load on the patient during the training.

The second current value may be calculated by multiplying a rated current of the motor by a predetermined number smaller than one. In this way, it is possible to prevent the rated current from being supplied to the motor for a long period. As a result, the training rod can be controlled without applying an excessive load on the patient.

In addition, it is possible to avoid that an excessive electric load is applied on a control unit of the training apparatus.

The training apparatus may further include an accumulated time measuring unit. The accumulated time measuring unit measures an accumulated time when the position difference during the first time period is a second threshold or higher and lower than the first threshold. The second threshold is less than the first threshold. In this case, the determination unit may determine an error when the accumulated time is a predetermined third time period or longer.

Because the accumulated time measuring unit measures the time period when the position difference generated during the first time period is the second threshold or higher and lower than the first threshold, it is possible to measure the time period while a slow position difference change continues (the accumulated time). In addition, because the determination unit determines an error when the accumulated time is the predetermined third time period or longer, the training can be continued for the slow position difference change until the third time period elapses. The second threshold is a threshold for determining that an excessive load is not applied on the limb of the patient. Therefore, an error occurred in this case can be appropriately used to cope with a difficulty level of the training program is so high that the patient cannot carry out the training program, or a prediction of a potential slow breakdown of a component in the apparatus. On the basis of this determination, the patient can carry out an appropriate training program in accordance with a symptom.

The training apparatus may further include an instruction generation unit and a motor drive unit. The instruction generation unit generates a speed instruction for controlling a speed of the motor in accordance with the training program. The motor drive unit drives the motor in accordance with the speed instruction. In addition, the speed instruction may include at least one of an acceleration instruction for accelerating the motor and a deceleration instruction for decelerating the motor. Further, the motor drive unit may drive the motor so that the position difference is accumulated and maintained when the acceleration instruction is executed.

When the motor is driven by using the speed instruction including at least the acceleration instruction or the deceleration instruction generated by the instruction generation unit, the motor can smoothly operate in accordance with the training program and a patient's operation. As a result, the patient can operate the training rod as intended.

In addition, when the motor drive unit drives the motor so that the position difference is accumulated and maintained when the acceleration instruction is executed, even if a position difference occurs in start and stop of the training rod by the patient, when executing the acceleration instruction that is apt to cause a position difference in a short period, in particular, the patient can continue the training using the training apparatus. In addition, because the position difference is accumulated and maintained, a state of the limb of the patient during the training can be detected on the basis of an accumulated amount of the position difference.

The speed instruction may further include a constant speed instruction. The constant speed instruction is an instruction for rotating the motor at a constant speed. In addition, the constant speed instruction is disposed before or after the acceleration instruction or the deceleration instruction. In addition, the motor drive unit may drive the motor so that the position difference is accumulated and maintained when the constant speed instruction is executed.

Because the speed instruction further includes the constant speed instruction, the motor can smoothly operate at a constant speed on the basis of the feedback current value even if the training rod operates with a large tilt angle. In addition, because the motor is driven so that the position difference is accumulated and maintained when the constant speed instruction is executed, the patient can continue the training using the training apparatus even if the training rod operates with a large tilt angle, for example, in which a relatively large motor torque is required, and a position difference is apt to occur.

The motor drive unit may drive the motor so as to follow only the speed instruction when the acceleration instruction and/or the constant speed instruction are executed. In this way, when the acceleration instruction is executed and/or when the constant speed instruction is executed, the motor can be driven regardless of the position difference. As a result, the patient can continue the training using the training apparatus even if the training rod operates with a large tilt angle, for example, in which a relatively large motor torque is required, and a position difference is apt to occur.

The instruction generation unit may further generate a position instruction for controlling the tilt angle of the training rod in accordance with the training program. In addition, the motor drive unit may drive the motor so as to follow the speed instruction and the position instruction when the deceleration instruction is executed.

In this way, the motor drive unit can control the motor so that the training rod can reach a target tilt angle instructed by the training program with a difference as small as possible. As a result, also when position information of the training rod is fed back as visual information to the patient, this position information can be appropriately used.

The motor drive unit may reset the accumulated position difference when the tilt angle of the training rod reaches a deceleration start position. Here, the reset of the accumulated position difference means to set the accumulated and maintained position difference to zero. In this way, when decelerating, it is possible to prevent an excessive increase of a motor speed based on the position instruction. As a result, the patient can carry out the training using the training apparatus.

Advantageous Effects

Because the temporal change difference of the position difference and the load amount necessary for the training rod to move the upper or lower limb can be correctly monitored, the apparatus can provide the patient with an appropriate rehabilitation. In addition, because the training rod can be appropriately controlled on the basis of the monitor information, an appropriate training program can be provided in accordance with a state of the patient.

DESCRIPTION OF EMBODIMENTS

1. First Embodiment

(1) Overall Structure of Training Apparatus

Figure 1:
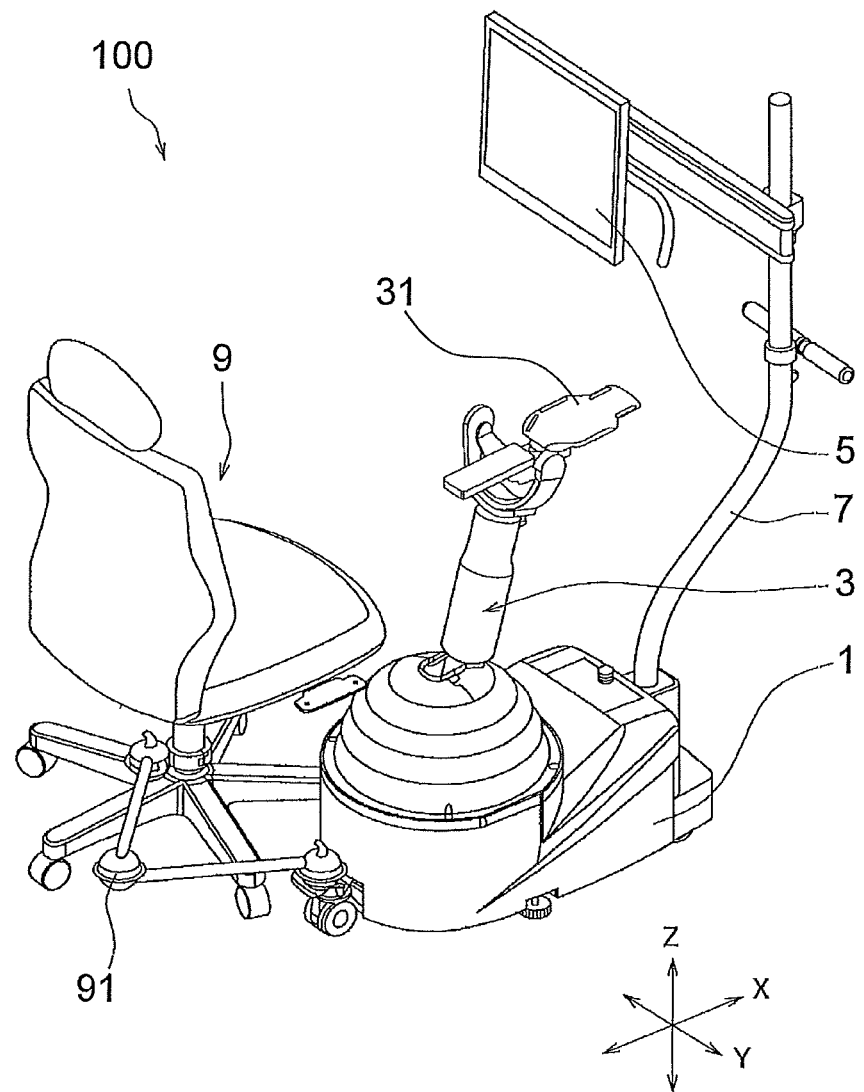
FIG. 1 is a diagram schematically illustrating a training apparatus.

An overall structure of a training apparatus 100 according to a first embodiment is described with reference to FIG. 1. FIG. 1 is a diagram schematically illustrating the training apparatus 100. The training apparatus 100 is a training apparatus for carrying out training aimed at motor function recovery of a limb of a patient in accordance with a predetermined training program.

Figure 2:
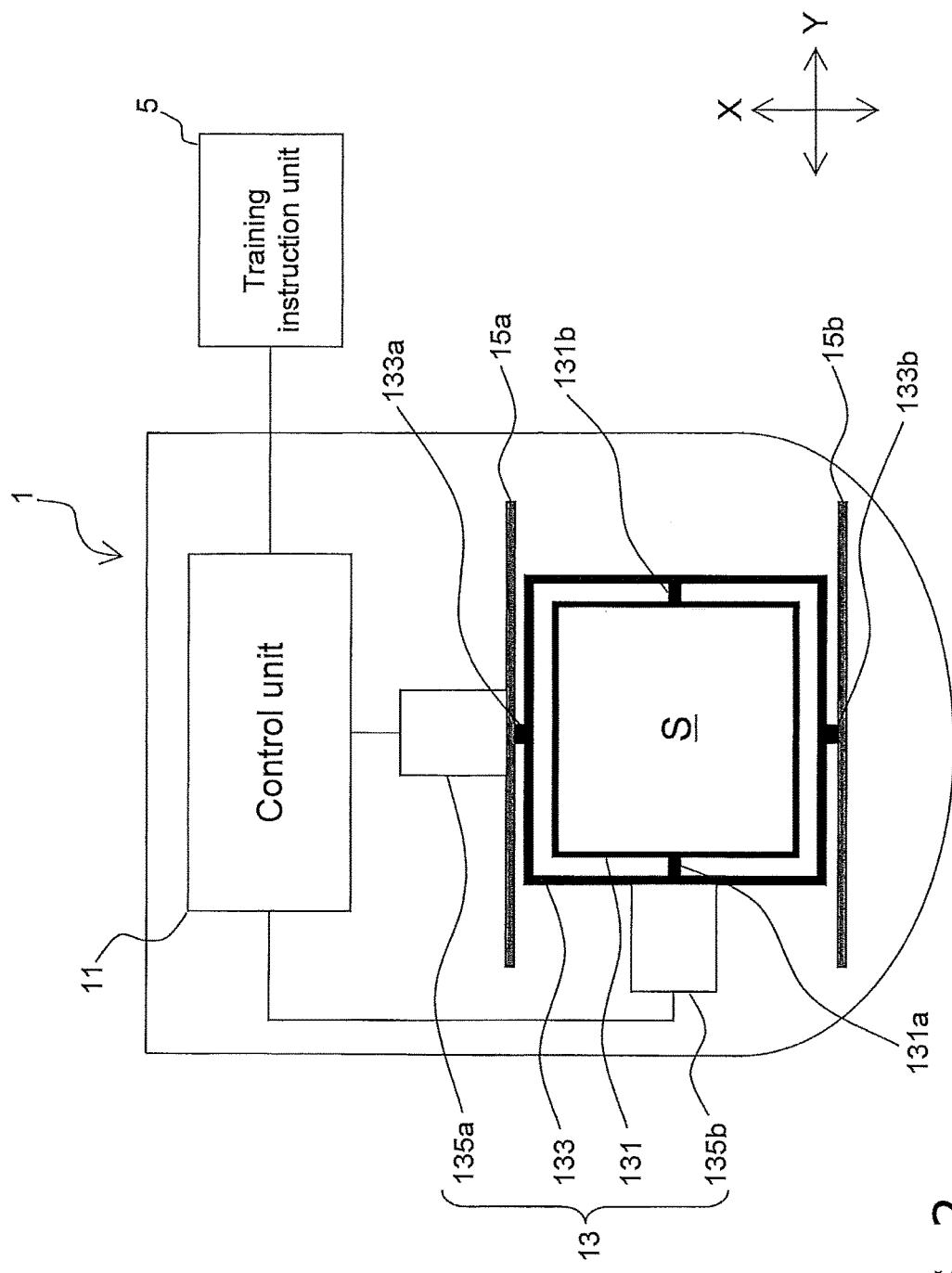
FIG. 2 is a diagram illustrating an overall structure of a control unit and a training rod tilt mechanism.

The training apparatus 100 includes mainly a fixed frame 1, a training rod 3, and a training instruction unit 5. The fixed frame 1 is placed on or in the vicinity of a floor on which the training apparatus 100 is installed. In addition, the fixed frame 1 constitutes a main body casing of the training apparatus 100. The training rod 3 is attached to the fixed frame 1 via a training rod tilt mechanism 13 (FIG. 2) disposed inside the fixed frame 1. As a result, the training rod 3 can be tilted by the training rod tilt mechanism 13 with at least one degree of freedom in an X-axis direction parallel to a longitudinal direction of the fixed frame 1 and in a Y-axis direction parallel to a width direction of the fixed frame 1 (FIGS. 1 and 2).

In addition, the training rod 3 may include an expansion/contraction mechanism (FIG. 3) inside for expanding and contracting the training rod 3 in a longitudinal axis direction. In this case, the training rod 3 can also expand and contract in the longitudinal direction of the training rod 3, and hence the training rod 3 can move with at least 2 degrees of freedom or 3 degrees of freedom in cooperation with the training rod tilt mechanism.

In addition, the training rod 3 includes a limb support member 31 (described later) disposed on an upper end portion of the training rod 3. When the limb of the patient is supported by the limb support member 31, the training rod 3 can move the limb of the patient. Alternatively, the patient can move the training rod 3 by himself/herself.

The training instruction unit 5 is fixed to the fixed frame 1 via a fixing member 7. The training instruction unit 5 executes a preset training program and transmits a training rod operation instruction to a control unit 11 (FIG. 2), for operating the training rod 3, as necessary. In addition, the training instruction unit 5 provides a training route and an actual training movement of the limb of the patient as visual or auditory information by the preset training program. In this way, the patient can carry out the training of the limb while feeding back the training movement set by the training program and the actual movement.

In addition, the training instruction unit 5 provides visual or auditory information for notifying the user that an error has occurred when a determination unit 1134 (FIGS. 7A to 7C) determines an error. In this way, the user can be notified about a status of the training apparatus 100, i.e., that an error has occurred, and/or about a cause or the like of the error.

Further, when the patient has moved the training rod 3 to reach a preset passing point (may also referred to as a target tilt angle) in the training route set by the training program, the training instruction unit 5 provides visual information and/or auditory information for notifying the user that the training program is accomplished. In this way, the user can know that the training rod 3 has been operated just in accordance with the training program. In addition, because the user is notified that the patient has moved the training rod 3 to reach the preset passing point by the visual or auditory information, the patient can maintain a motivation to continue the training.

As the training instruction unit 5, an integrated computer system can be used, which includes a display device such as a liquid crystal display, a central processing unit (CPU), a storage device such as a random access memory (RAM), a read only memory (ROM), a hard disk and a solid state drive (SSD), and an input device such as a touch panel as necessary. In addition, the training instruction unit 5 may be constituted of a separate display device and other computer system. In this case, only the display device is fixed to the fixed frame 1 via the fixing member 7.

The training program executed by the training instruction unit 5 has five training modes, for example, including (i) a guided mode, (ii) an initiated mode, (iii) a step initiated mode, (iv) a follow assist mode, and (v) a free mode. The guided mode is a training mode in which the training rod 3 moves the limb in a predetermined direction at a constant speed regardless of a movement of the limb of the patient. The initiated mode is a training mode in which the training rod 3 moves the limb of the patient in a direction of the predetermined training route at a constant speed when detecting a force that the patient intends to move the training rod 3 by the limb in a correct direction at an initial movement position with respect to the training route preset by the training program (also referred to as a force sensing trigger). The step initiated mode is a training mode in which the training rod 3 moves the limb of the patient by a constant distance in the training route when detecting the force sensing trigger at a predetermined point in the training route of the training rod 3. The follow assist mode is a training mode in which the force sensing trigger is detected every predetermined period, and a speed of the training rod 3 is changed in accordance with a level of the detected force sensing trigger. The free mode is a training mode in which the training rod 3 is moved so as to follow a movement of the limb of the patient.

In addition, the training apparatus 100 may further include a chair 9 for the patient to sit during the training. The chair 9 is connected to the fixed frame 1 via the chair connecting member 91, and hence stability of the training apparatus 100 can be secured. In addition, because the chair connecting member 91 is reproducibly fixed, the patient can carry out the training every time at the same position.

(2) Structure of Control Unit and Training Rod Tilt Mechanism

I. Overall Structure

Next, an overall structure of the control unit 11 and the training rod tilt mechanism 13 is described with reference to FIG. 2. FIG. 2 is a diagram illustrating an overall structure of the control unit 11 and the training rod tilt mechanism 13 disposed in the fixed frame 1.

Figure 3:
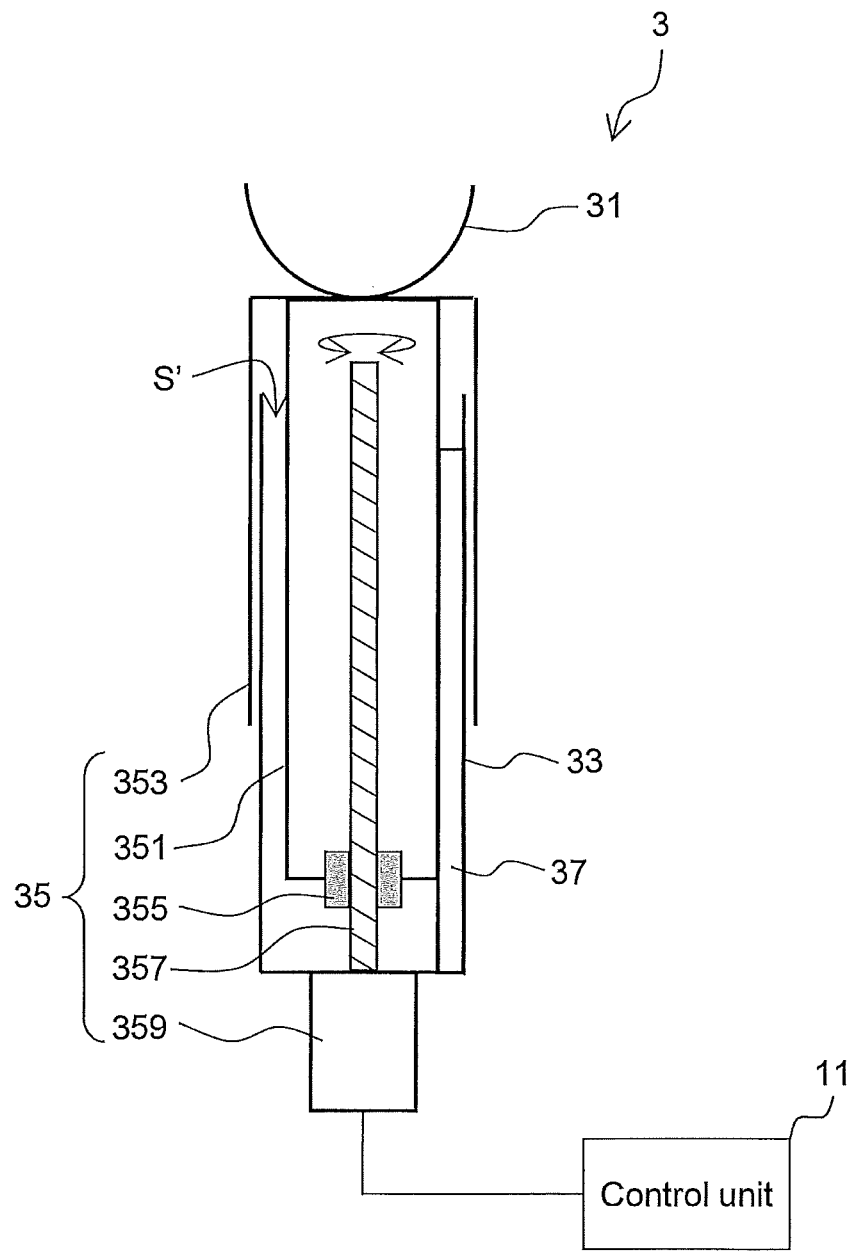
FIG. 3 is a diagram illustrating a structure of a training rod.

The control unit 11 and the training rod tilt mechanism 13 are disposed in the fixed frame 1. The control unit 11 is connected to the training instruction unit 5 in a manner capable of transmitting and receiving signals. The control unit 11 receives the training rod operation instruction transmitted from the training instruction unit 5. In addition, the control unit 11 is electrically connected to an X-axis direction tilt motor 135b (described later), a Y-axis direction tilt motor 135a (described later), and an expansion/contraction motor 359 (FIG. 3). Accordingly, the control unit 11 drives the above-mentioned three motors on the basis of the training rod operation instruction. Note that structure and operation of the control unit 11 will be described later in detail.

The training rod tilt mechanism 13 is attached to the fixed frame 1 in a manner capable of tilting via training rod tilt mechanism fixing members 15a and 15b fixed to the fixed frame 1. In this way, the training rod tilt mechanism 13 can tilt the training rod 3 in the X-axis direction and in the Y-axis direction (with 2 degrees of freedom). Hereinafter, a structure of the training rod tilt mechanism 13 is described in detail.

Note that the training rod tilt mechanism 13 may be configured to tilt the training rod 3 only in the X-axis direction or in the Y-axis direction (with one degree of freedom). Alternatively, the training rod tilt mechanism 13 may be selectable whether to tilt the training rod 3 with one degree of freedom or with 2 degrees of freedom.

II. Structure of Training Rod Tilt Mechanism

Here, a structure of the training rod tilt mechanism 13 of this embodiment is described with reference to FIG. 2. The training rod tilt mechanism 13 tilts the training rod 3 in the X-axis direction and in the Y-axis direction by a "gimbal" mechanism that moves two axes. In addition, the training rod tilt mechanism 13 of this embodiment can also tilt simultaneously both in the X-axis direction and in the Y-axis direction (i.e., in a diagonal direction). Here, the X-axis direction is a horizontal direction parallel to the longitudinal direction of the fixed frame 1 in FIG. 2. The Y-axis direction is a horizontal direction parallel to the width direction of the fixed frame 1 in FIG. 2.

The training rod tilt mechanism 13 includes an X-axis direction tilt member 131 and a Y-axis direction tilt member 133, as well as the X-axis direction tilt motor 135b and the Y-axis direction tilt motor 135a respectively corresponding to the tilt members.

Further, when the training rod tilt mechanism 13 tilts the training rod 3 with one degree of freedom, it is sufficient that the training rod tilt mechanism 13 includes only the X-axis direction tilt member 131 and the X-axis direction tilt motor 135b, or the Y-axis direction tilt member 133 and the Y-axis direction tilt motor 135a. Alternatively, even if the training rod tilt mechanism 13 includes the above-mentioned two members and two motors, the training rod tilt mechanism 13 can tilt the training rod 3 with one degree of freedom by disabling one combination of the member and the motor.

The X-axis direction tilt member 131 is disposed inside a space of the Y-axis direction tilt member 133. In addition, the X-axis direction tilt member 131 includes two shafts 131a and 131b extending outside from two side surfaces each having normal line parallel to the Y-axis. The two shafts 131a and 131b are supported respectively by the two side surfaces each having normal line parallel to the Y-axis of the Y-axis direction tilt member 133 in a manner capable of rotating the X-axis direction tilt member 131 about the Y-axis. In this way, the X-axis direction tilt member 131 can change an angle between the training rod 3 fixed to the X-axis direction tilt member 131 and the X-axis. Here, changing the angle between the training rod 3 and the X-axis may be referred to as "tilting in the X-axis direction".

Note that the training rod 3 is fixed to the X-axis direction tilt member 131 in a state where a part of the training rod 3 is inserted in a space S of the X-axis direction tilt member 131.

In the same manner, the Y-axis direction tilt member 133 includes two shafts 133a and 133b extending outside from two side surfaces each having normal line parallel to the X-axis. The two shafts 133a and 133b are supported respectively by the training rod tilt mechanism fixing members 15a and 15b in a manner capable of rotating the Y-axis direction tilt member 133 about the X-axis. In this way, the Y-axis direction tilt member 133 can rotate about the X-axis with respect to the training rod tilt mechanism fixing members 15a and 15b. As a result, the Y-axis direction tilt member 133 can change an angle between the training rod 3 fixed to the X-axis direction tilt member 131 and the Y-axis. Here, changing the angle between the training rod 3 and the Y-axis may be referred to as "tilting in the Y-axis direction".

In this way, the Y-axis direction tilt member 133 tilts the training rod 3 in the Y-axis direction, and the X-axis direction tilt member 131 tilts the training rod 3 in the X-axis direction. Accordingly, the training rod tilt mechanism 13 can tilt the training rod 3 with two-dimensional degrees of freedom.

Further, although the X-axis direction tilt member 131 is disposed inside the space of the Y-axis direction tilt member 133 in FIG. 2, it is possible to modify the design so that the X-axis direction tilt member 131 is disposed outside the space of the Y-axis direction tilt member 133 so as to tilt the corresponding member.

The Y-axis direction tilt motor 135a is fixed to the training rod tilt mechanism fixing member 15a. In addition, an output rotation shaft of the Y-axis direction tilt motor 135a is connected, via a speed reduction mechanism (not shown), to the shaft 133a extending from the Y-axis direction tilt member 133, so as to rotate the shaft 133a. Accordingly, the Y-axis direction tilt motor 135a rotates the Y-axis direction tilt member 133 about the X-axis. Further, the Y-axis direction tilt motor 135a is electrically connected to the control unit 11. Accordingly, the Y-axis direction tilt motor 135a can tilt the training rod 3 in the Y-axis direction by control by the control unit 11.

The X-axis direction tilt motor 135b is fixed to the surface of the Y-axis direction tilt member 133 that pivotally supports a shaft 131a extending from the X-axis direction tilt member 131 among four side surfaces of the Y-axis direction tilt member 133. In addition, an output rotation shaft of the X-axis direction tilt motor 135b is connected to the shaft 131a extending from the X-axis direction tilt member 131 via a speed reduction mechanism (not shown) so as to rotate the shaft 131a. Accordingly, the X-axis direction tilt motor 135b can rotate the X-axis direction tilt member 131 about the Y-axis. Further, the X-axis direction tilt motor 135b is electrically connected to the control unit 11. Accordingly, the X-axis direction tilt motor 135b can tilt the training rod 3 in the X-axis direction by control by the control unit 11.

In this way, the Y-axis direction tilt motor 135a and the X-axis direction tilt motor 135b tilt the training rod 3 respectively in the X-axis direction and in the Y-axis direction with one degree of freedom by control by the control unit 11. In other words, because the X-axis direction tilt motor 135b and the Y-axis direction tilt motor 135a are provided, the training rod 3 can be controlled in a two-dimensional manner.

As the Y-axis direction tilt motor 135a and the X-axis direction tilt motor 135b, an electric motor such as a servo motor or a brush-less motor can be used, for example.

(3) Structure of Training Rod

I. Overall Structure

Next, a structure of the training rod 3 is described with reference to FIG. 3. First, an overall structure of the training rod 3 is described. FIG. 3 is a diagram illustrating a structure of the training rod 3. The training rod 3 includes the limb support member 31, a fixed stay 33, and an expansion/contraction mechanism 35. The limb support member 31 is fixed to an upper end portion of a cover 353 (described later) of the expansion/contraction mechanism 35. The limb support member 31 is a member supporting the limb of the patient. The fixed stay 33 constitutes a main body of the training rod 3. In addition, the fixed stay 33 has a space S' for housing a movable stay 351 (described later) of the expansion/contraction mechanism 35. Further, the fixed stay 33 includes a fixing member (not shown) for fixing the training rod 3 to the X-axis direction tilt member 131 of the training rod tilt mechanism 13. When the fixed stay 33 is fixed to the X-axis direction tilt member 131 with the fixing member of the fixed stay 33, the training rod 3 is fixed to the training rod tilt mechanism 13.

The expansion/contraction mechanism 35 is provided to the fixed stay 33 in a movable manner along the longitudinal direction of the fixed stay 33. In this way, the training rod 3 can expand and contract in the longitudinal direction of the training rod 3. Hereinafter, a structure of the expansion/contraction mechanism 35 is described in detail.

II. Structure of Expansion/Contraction Mechanism

Next, a structure of the expansion/contraction mechanism 35 is described with reference to FIG. 3. The expansion/contraction mechanism 35 includes the movable stay 351, the cover 353, a nut 355, a threaded shaft 357 (described later), and an expansion/contraction motor 359.

The movable stay 351 is inserted in the space S' formed in the fixed stay 33. In addition, the movable stay 351 includes a slide unit (not shown). This slide unit is slidably engaged with a guide rail 37 provided on an inner wall of the fixed stay 33. As a result, the movable stay 351 can move along the guide rail 37 in the space S' formed in the fixed stay 33. The cover 353 is fixed to the upper end portion of the movable stay 351. In this way, the cover 353 can move in the longitudinal direction of the training rod 3 in accordance with movement of the movable stay 351. In addition, the cover 353 includes a limb support member 31 on the upper end portion. Accordingly, the cover 353 can move the limb support member 31 in the longitudinal direction of the fixed stay 33.

The nut 355 is attached to a bottom portion of the movable stay 351. The nut 355 is engaged with the threaded shaft 357. The threaded shaft 357 is a thread member elongated in parallel to the longitudinal direction of the fixed stay 33. In addition, the threaded shaft 357 is engaged with the nut 355. Accordingly, when the threaded shaft 357 rotates, the nut 355 moves along the longitudinal direction of the threaded shaft 357 (namely, the longitudinal direction of the fixed stay 33 (the longitudinal axis direction)).

As described above, because the nut 355 is fixed to the bottom portion of the movable stay 351, when the nut 355 moves along the longitudinal direction of the threaded shaft 357, the movable stay 351 can move along the longitudinal direction of the fixed stay 33.

The expansion/contraction motor 359 is fixed to a bottom portion of the fixed stay 33. In addition, an output rotation shaft of the expansion/contraction motor 359 is connected to an end portion in the longitudinal direction of the threaded shaft 357 so as to rotate the threaded shaft 357 about the axis. Further, the expansion/contraction motor 359 is electrically connected to the control unit 11. Accordingly, the expansion/contraction motor 359 can rotate the threaded shaft 357 about the axis of the threaded shaft 357 by control by the control unit 11.

As described above, the nut 355 is engaged with the threaded shaft 357, and hence the nut 355 can move along the longitudinal direction of the threaded shaft 357 in accordance with rotation of the threaded shaft 357. Accordingly, the movable stay 351 can move along the longitudinal direction of the fixed stay 33 (longitudinal axis direction) in accordance with rotation of the expansion/contraction motor 359.

(4) Structure of Control Unit

I. Overall Structure

Figure 4:
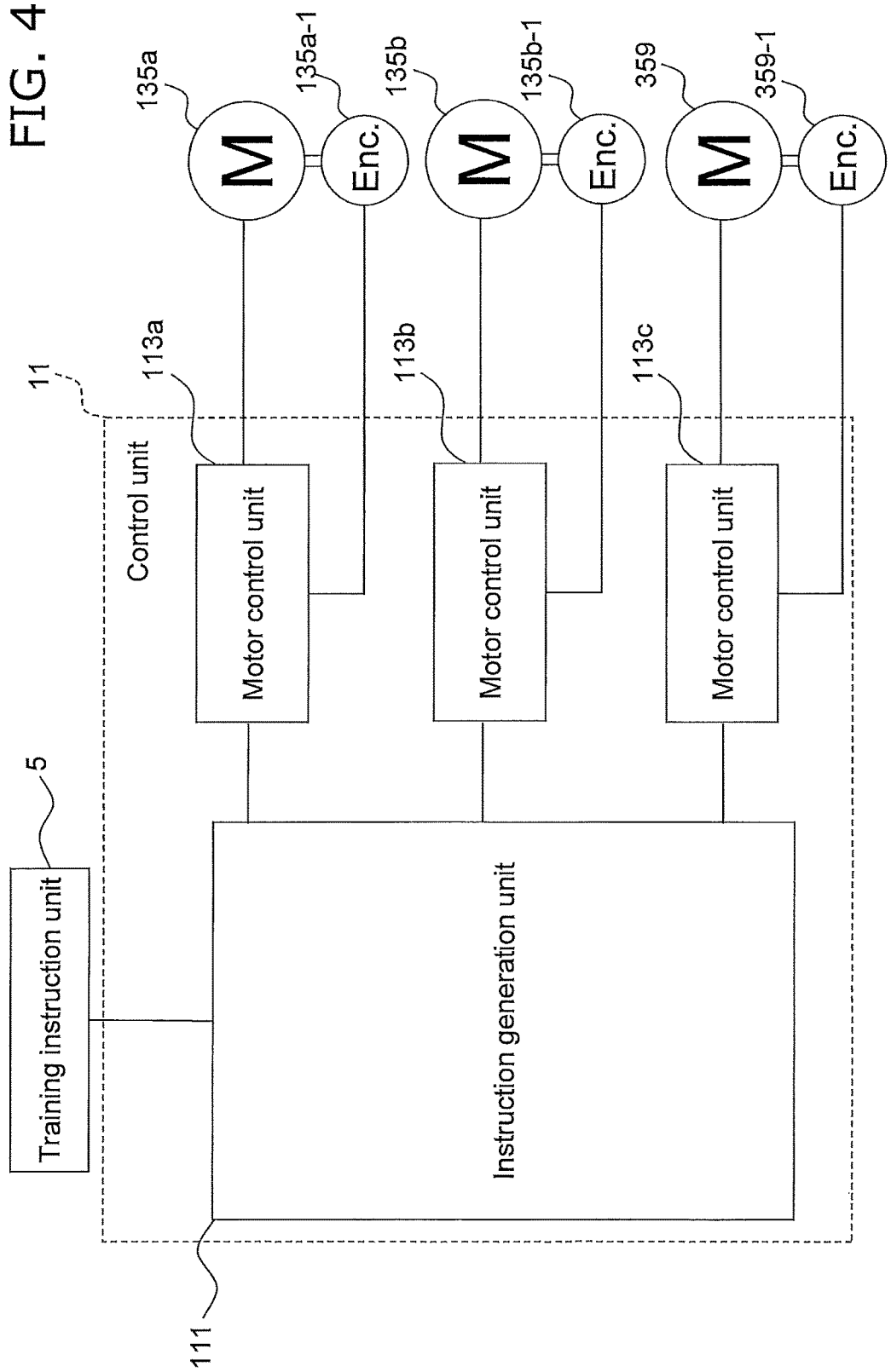
FIG. 4 is a diagram illustrating an overall structure of the control unit.

Next, an overall structure of the control unit 11 is described with reference to FIG. 4. FIG. 4 is a diagram illustrating an overall structure of the control unit 11. As the control unit 11, it is possible to use a microcomputer system, for example, which includes a CPU, a storage device such as a RAM, a ROM, a hard disk drive, and an SSD, an interface for converting an electric signal, and the like. In addition, a part or a whole of functions of the control unit 11 described below may be realized by a program that can be executed by the microcomputer system. In addition, the program may be stored in the storage device of the microcomputer system. Further, a part or a whole of functions of the control unit 11 may be realized by a custom IC or the like.

The control unit 11 includes an instruction generation unit 111, and motor control units 113a, 113b, and 113c.

The instruction generation unit 111 is connected to the training instruction unit 5 and the motor control units 113a, 113b, and 113c in a manner capable of transmitting and receiving signals. The instruction generation unit 111 generates instructions for the motor control units 113a, 113b, and 113c to respectively drive the Y-axis direction tilt motor 135a, the X-axis direction tilt motor 135b, and the expansion/contraction motor 359 on the basis of the training rod operation instruction transmitted from the training instruction unit 5.

The instructions generated by the instruction generation unit 111 include a speed instruction and a position instruction. The speed instruction is an instruction for controlling rotation speed of the motor (an amount of change of the tilt angle or the expansion/contraction length of the training rod 3 per unit time). In addition, the position instruction is an instruction for controlling the tilt angle or the expansion/contraction length of the training rod 3.

As described later, when each of the motor control units 113a, 113b, and 113c controls each of the motors on the basis of the speed instruction, the motor is controlled to follow the speed instructed by the speed instruction. In other words, if there is a difference (speed difference) between the speed instructed by the speed instruction and the actual rotation speed of the motor, each of the motor control units 113a, 113b, and 113c controls the motors so as to eliminate the speed difference.

On the other hand, when each of the motor control units 113a, 113b, and 113c controls the motors on the basis of the position instruction, the motors are controlled to allow the tilt angle or the expansion/contraction length of the training rod 3 to follow the tilt angle instructed by the position instruction (instructed tilt angle) or the expansion/contraction length instructed by the position instruction (instructed expansion/contraction length). In other words, if there is a difference (position difference) between the tilt angle instructed by the position instruction and the actual tilt angle of the training rod 3, or between the expansion/contraction length instructed by the position instruction and the actual expansion/contraction length of the training rod 3, each of the motor control units 113*a*, 113*b*, and 113*c* controls the motor so as to eliminate the position difference.

Note that the speed instruction and the position instruction generated by the instruction generation unit 111 are functions of time. On the other hand, the training rod operation instruction transmitted from the training instruction unit 5 includes at least information of the tilt angle to which the training rod 3 should be moved (target position information) and information of the amount of change of the tilt angle or the expansion/contraction length of the training rod 3 per unit time (the tilt angle speed or the expansion/contraction length speed) (target speed information), and further includes information of an acceleration rate for the tilt angle speed or the expansion/contraction length speed of the training rod 3 to reach a desired tilt angle speed or expansion/contraction length speed (acceleration rate information) and information of a deceleration rate for stopping the moving training rod 3 (deceleration rate information).

In other words, the training rod operation instruction as a base for generating the speed instruction and the position instruction does not include information of time. However, the training rod operation instruction includes information of distance (corresponding to the target position information) and information of speed (corresponding to the target speed information), and further includes information of acceleration rate (corresponding to the acceleration rate information and the deceleration rate information). Accordingly, the information of time can be derived from these information.

Thus, the instruction generation unit 111 can generate the speed instruction and the position instruction as functions of time, by calculating with appropriate combination of the target position information and the target speed information, as well as the acceleration rate information and the deceleration rate information, included in the training rod operation instruction.

Figure 5A:
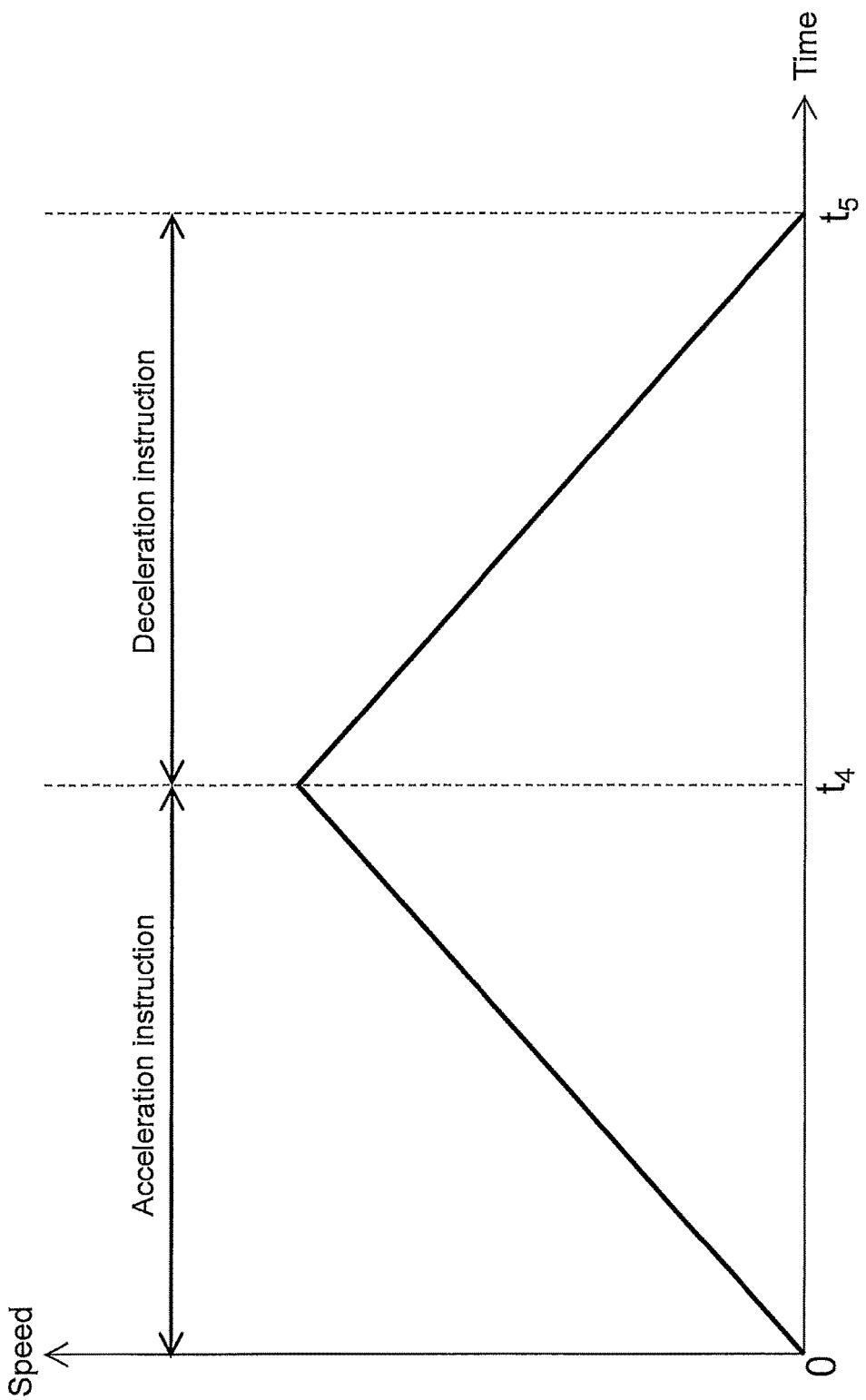
FIG. 5A is a graph illustrating a triangular speed locus type speed instruction on a time-speed coordinate plane.
Figure 5B:
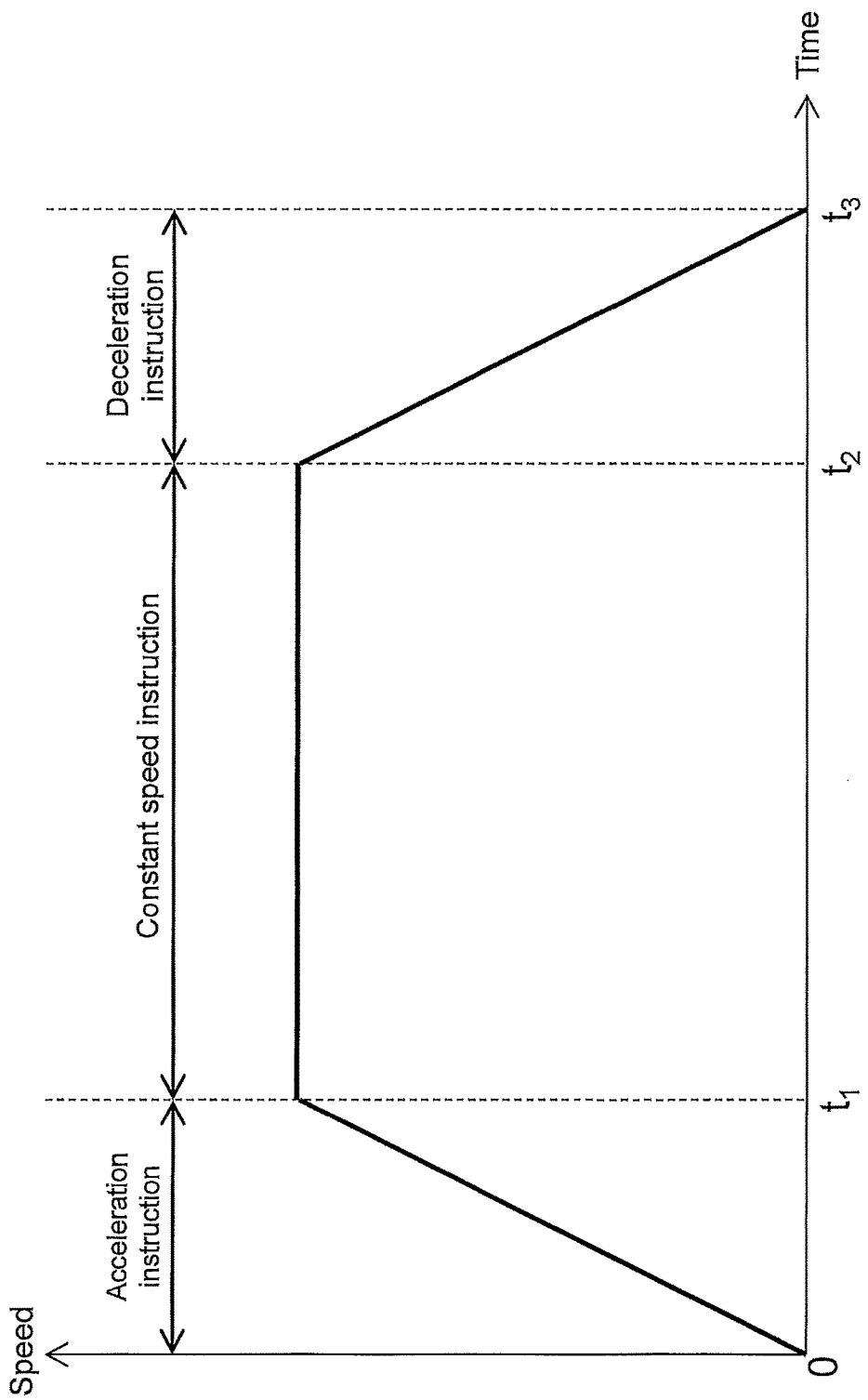
FIG. 5B is a graph illustrating a trapezoidal speed locus type speed instruction on a time-speed coordinate plane.

In addition, the speed instructions generated by the instruction generation unit 111 include two types of speed instructions as illustrated in FIGS. 5A and 5B. One of them is the speed instruction as illustrated in FIG. 5A, which includes only an acceleration instruction for accelerating the motor at a constant acceleration rate and a deceleration instruction for decelerating the motor at a constant deceleration rate. This speed instruction can be expressed as a graph having a triangular shape in a coordinate system in which the horizontal axis represents time, while the vertical axis represents speed. Accordingly, this speed instruction may be referred to as a triangular speed locus type speed instruction. The case where the speed instruction becomes the triangular speed locus type is, for example, a case where a moving distance of the training rod 3 is short when moving from a current tilt angle of the training rod 3 to a target tilt angle of the training rod 3 instructed by the training instruction unit 5, a case where the acceleration rate and the deceleration rate of the motor instructed by the training rod operation instruction are small, or the like.

In this way, because the speed instruction includes the acceleration instruction and the deceleration instruction, the motor control units 113*a*, 113*b*, and 113*c* can smoothly control the motors.

The other type is the speed instruction as illustrated in FIG. 5B, which includes, in addition to the acceleration instruction and the deceleration instruction, a constant speed instruction for rotating the motor at a constant speed. This speed instruction can be expressed as a graph having a trapezoidal shape in a coordinate system in which the horizontal axis represents time, while the vertical axis represents speed. Accordingly, this speed instruction may be referred to as a trapezoidal speed locus type speed instruction. The case where the speed instruction becomes the trapezoidal speed locus is, for example, a case where a moving distance of the training rod 3 is long when moving from a current tilt angle of the training rod 3 to a target tilt angle of the training rod 3 instructed by the training instruction unit 5, a case where the acceleration rate and the deceleration rate of the motor are large, or the like.

In this way, because the speed instruction further includes the constant speed instruction, the motor control units 113*a*, 113*b*, and 113*c* can smoothly control the motors even if the training rod 3 moves with a large tilt angle.

Figure 6:
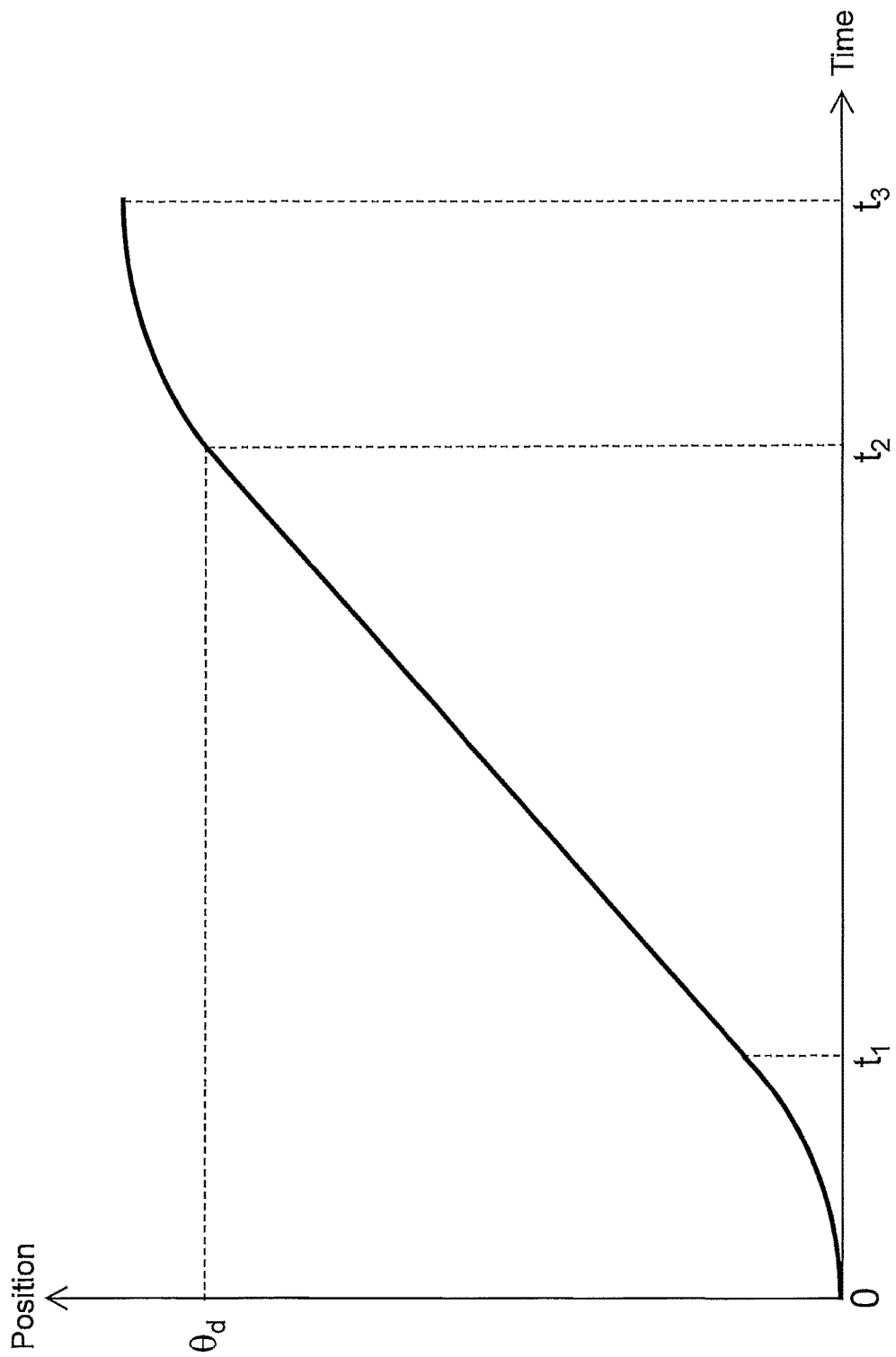
FIG. 6 is a graph illustrating a position instruction on a time-tilt angle coordinate plane.

On the other hand, the position instruction generated by the instruction generation unit 111 has a shape as illustrated in FIG. 6 in a coordinate system in which the horizontal axis represents time, while the vertical axis represents position (tilt angle). The position instruction corresponds to an integrated value of the speed instruction over time. The position instruction illustrated in FIG. 6 is a position instruction corresponding to the trapezoidal speed locus type speed instruction illustrated in FIG. 5B. Accordingly, in the trapezoidal speed locus type speed instruction, the position instruction has a downward-convex parabola shape with a vertex at time point 0 in a period between time points 0 to $t_1$ (during an acceleration instruction interval) while the speed increases with a positive gradient. In a period between time points $t_1$ and $t_2$ (a constant speed instruction interval) until the speed becomes a line parallel to a horizontal axis in the speed instruction, the position instruction increases linearly with a positive gradient. Further, in a period between time points $t_2$ and $t_3$ (during a deceleration instruction interval) while the speed decreases with a negative gradient in the speed instruction, the position instruction has an upward-convex parabola shape with a vertex at time point $t_3$.

The motor control units 113*a*, 113*b*, and 113*c* are connected to the instruction generation unit 111 in a manner capable of transmitting and receiving signals. Accordingly, the motor control units 113*a*, 113*b*, and 113*c* can receive the speed instruction and the position instruction from the instruction generation unit 111. In addition, the motor control units 113*a*, 113*b*, and 113*c* are electrically connected to the Y-axis direction tilt motor 135*a*, the X-axis direction tilt motor 135*b*, and the expansion/contraction motor 359, respectively. Accordingly, the motor control units 113*a*, 113*b*, and 113*c* can control the motors in accordance with the speed instruction and/or the position instruction.

Further, the motor control units 113*a*, 113*b*, and 113*c* are connected to a first rotation information detection sensor 135*a*-1 for the Y-axis direction tilt motor 135*a*, a second rotation information detection sensor 135*b*-1 for the X-axis direction tilt motor 135*b*, and a third rotation information detection sensor 359-1 for the expansion/contraction motor 359, respectively, in a manner capable of transmitting and receiving signals.

The first rotation information detection sensor 135*a*-1, the second rotation information detection sensor 135*b*-1, and the third rotation information detection sensor 359-1 are usually fixed to the output rotation shaft of the Y-axis direction tilt motor 135*a*, the output rotation shaft of the X-axis direction tilt motor 135*b*, and the output rotation shaft of the expansion/contraction motor 359, respectively. In this way, the first rotation information detection sensor 135*a*-1, the second rotation information detection sensor 135*b*-1, and the third rotation information detection sensor 359-1 can output an amount of rotation of the Y-axis direction tilt motor 135*a*, an amount of rotation of the X-axis direction tilt motor 135*b*, and an amount of rotation of the expansion/contraction motor 359, respectively. As the first rotation information detection sensor 135*a*-1, the second rotation information detection sensor 135*b*-1, and the third rotation information detection sensor 359-1, it is possible to use sensors that can measure an amount of rotation of the output rotation shaft of the motor. As such the sensor, for example, an encoder such as an incremental type encoder or an absolute type encoder can be appropriately used. When encoders are used as the sensors, the first rotation information detection sensor 135*a*-1, the second rotation information detection sensor 135*b*-1, and the third rotation information detection sensor 359-1 output pulse signals corresponding to amounts of rotation of the Y-axis direction tilt motor 135*a*, an amount of rotation of the X-axis direction tilt motor 135*b*, and an amount of rotation of the expansion/contraction motor 359, respectively.

In this way, because the motor control units 113*a*, 113*b*, and 113*c* are connected to the first rotation information detection sensor 135*a*-1, the second rotation information detection sensor 135*b*-1, and the third rotation information detection sensor 359-1, respectively, for measuring amounts of rotation of the output rotation shafts of the motors, the motor control units 113*a*, 113*b*, and 113*c* can control the motors in consideration of actual amounts of rotation of the motors.

Next, the motor control units 113*a*, 113*b*, and 113*c* are described in detail. In the following description, the motor control unit 113*a* is exemplified and described. It is because other motor control units 113*b* and 113*c* have the same structure and the same function as the motor control unit 113*a*.

II. Structure of Motor Control Unit

Figure 7A:
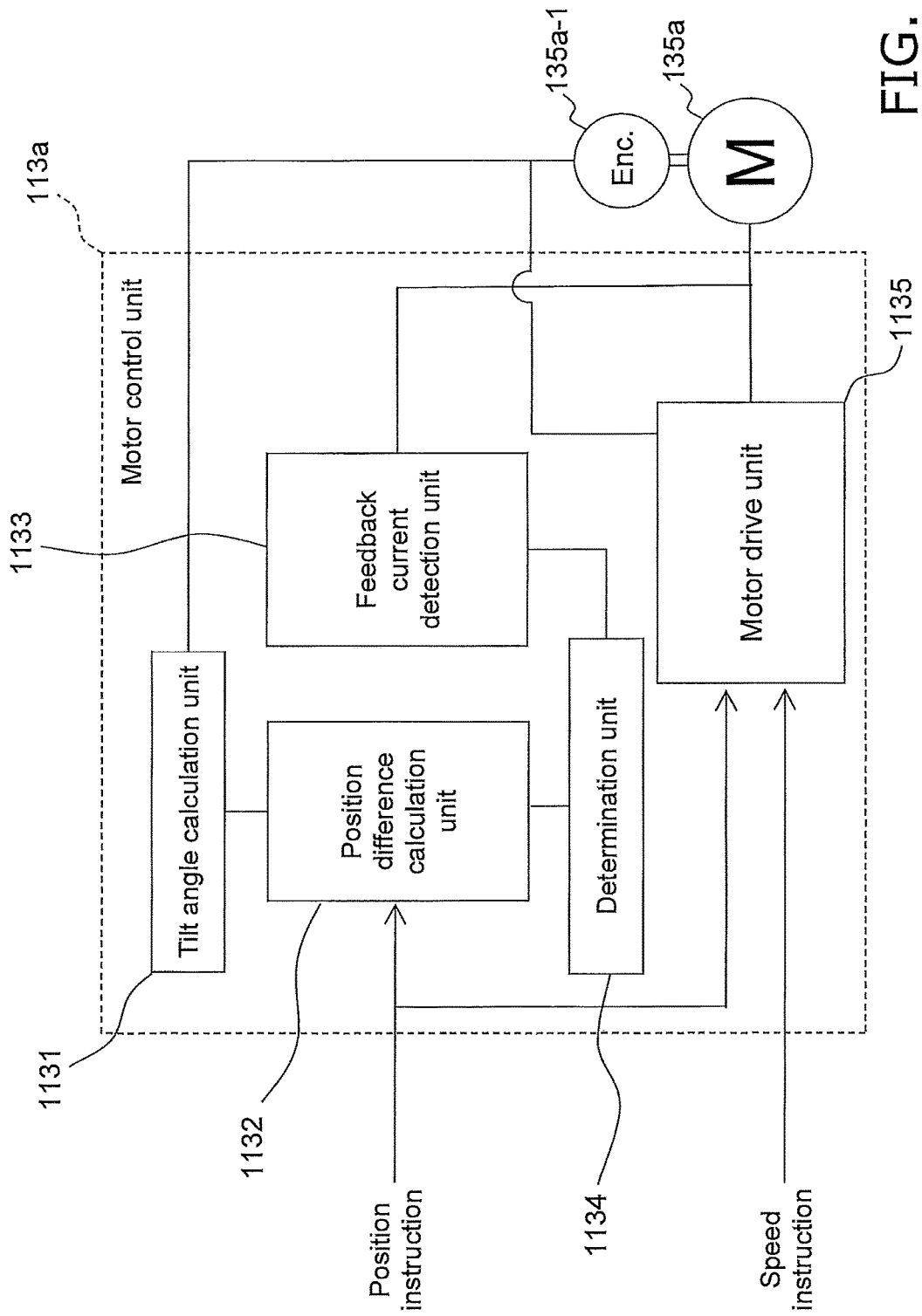
FIG. 7A is a diagram illustrating a basic structure of a motor control unit.

A structure of the motor control unit 113*a* is described with reference to FIG. 7A. FIG. 7A is a diagram illustrating a basic structure of the motor control unit 113*a*.

The motor control unit 113*a* includes a tilt angle calculation unit 1131, a position difference calculation unit 1132, a feedback current detection unit 1133, the determination unit 1134, and a motor drive unit 1135.

The tilt angle calculation unit 1131 is connected to the first rotation information detection sensor 135*a*-1 in a manner capable of transmitting and receiving signals. In this way, the pulse signal output corresponding to the amount of rotation of the output rotation shaft of the Y-axis direction tilt motor 135*a* measured by the first rotation information detection sensor 135*a*-1 is input to the tilt angle calculation unit 1131. Further, the tilt angle calculation unit 1131 calculates a tilt angle of the training rod 3 on the basis of the number of pulses included in the pulse signal output from the first rotation information detection sensor 135*a*-1.

The position difference calculation unit 1132 is connected to the tilt angle calculation unit 1131 in a manner capable of transmitting and receiving signals. In this way, the tilt angle of the training rod 3 calculated by the tilt angle calculation unit 1131 is input to the position difference calculation unit 1132. In addition, the position difference calculation unit 1132 is connected to the instruction generation unit 111 in a manner capable of transmitting and receiving signals. In this way, the position instruction generated by the instruction generation unit 111 is input to the position difference calculation unit 1132.

The position difference calculation unit 1132 calculates a difference between the actual tilt angle of the training rod 3 calculated by the tilt angle calculation unit 1131 and the tilt angle of the training rod 3 instructed by the position instruction (instructed tilt angle), as the position difference. In addition, the position difference calculation unit 1132 calculates the position difference every preset first time period $T_1$. Note that the first time period $T_1$ that determines the timing for calculating the position difference may be arbitrarily settable as necessary.

The feedback current detection unit 1133 is electrically connected to an output of the motor drive unit 1135 (described later). In this way, the feedback current detection unit 1133 can detect a current value of a feedback current I output from the motor drive unit 1135 to the Y-axis direction tilt motor 135*a*. In this case, as the feedback current detection unit 1133, it is possible to use a device capable of measuring current flowing in a winding of the motor. For instance, as the feedback current detection unit 1133, it is possible to use a shunt resistor, a cramp current meter, a current sense transformer, or the like.

Figure 8:
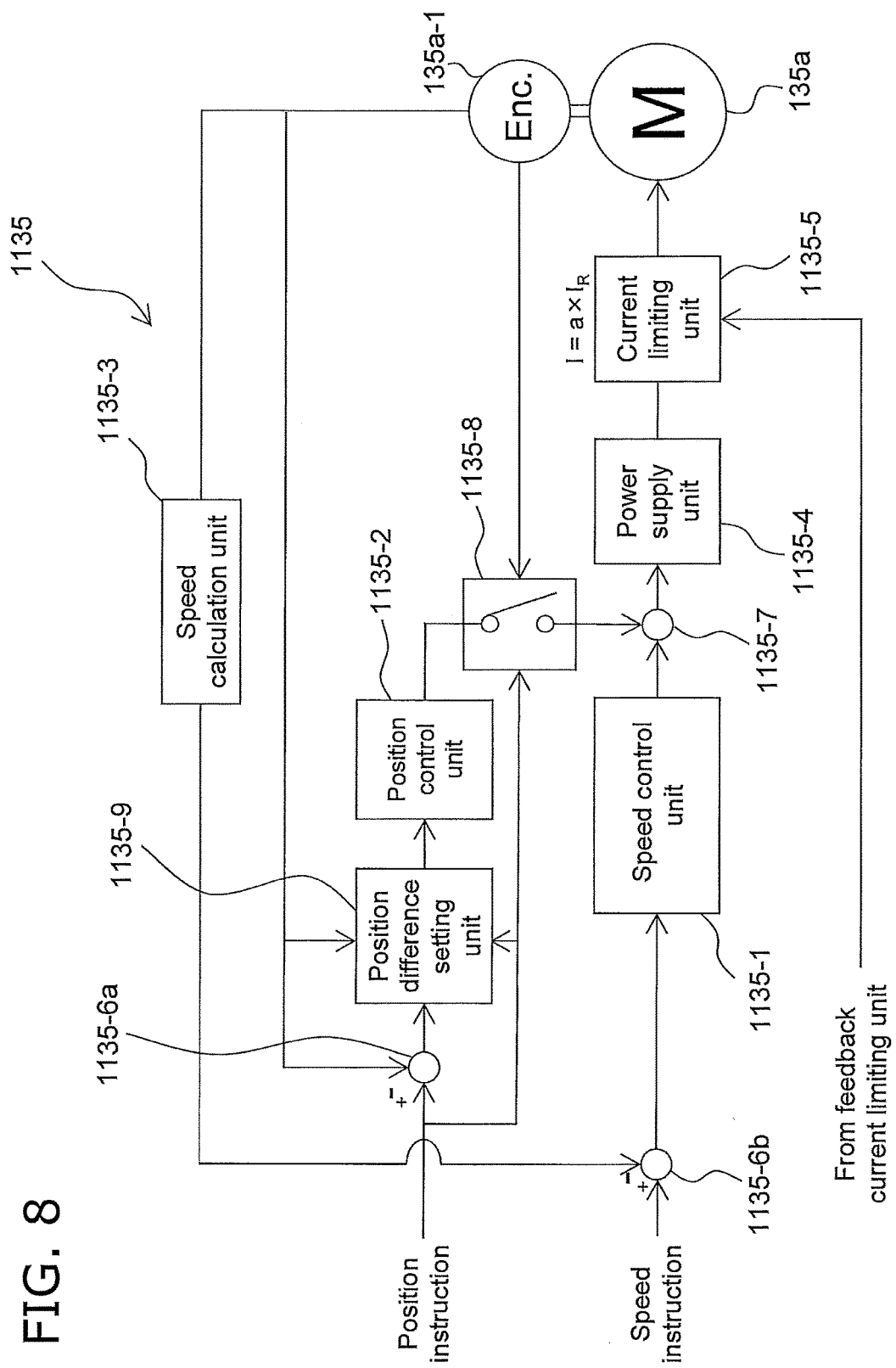
FIG. 8 is a diagram illustrating a structure of a motor drive unit.

Alternatively, the feedback current detection unit 1133 may detect a signal value of a first control amount and/or a second control amount output from a speed control unit 1135-1 (FIG. 8) and/or a position control unit 1135-2 (FIG. 8) for controlling a power supply unit 1135-4 (FIG. 8). In this case, the feedback current detection unit 1133 is connected to an input of the power supply unit 1135-4 of the motor drive unit 1135 (FIG. 8) in a manner capable of transmitting and receiving signals. In this case, the feedback current detection unit 1133 detects a combined control amount of the first control amount and the second control amount output from a combining unit 1135-7 (FIG. 8). In this way, the feedback current detection unit 1133 can predict the current value of the feedback current I without a device for measuring current flowing in the winding of the motor.

In addition, the feedback current detection unit 1133 includes a decision unit (not shown) for deciding whether or not the current value of the feedback current I is a first current value $I_1$ or higher.

The determination unit 1134 is connected to the position difference calculation unit 1132 and the feedback current detection unit 1133 in a manner capable of transmitting and receiving signals. The determination unit 1134 determines (i) whether or not a position difference generated per the first time period $T_1$ (described later) calculated by the position difference calculation unit 1132 is a first threshold $\varphi_1$ (described later) or higher, and (ii) whether or not a current value of the feedback current I detected by the feedback current detection unit 1133 is kept the first current value $I_1$ (described later) for a second time period $T_2$ (described later) or longer. Further, if the above-mentioned condition (i) or (ii) is "true", an error is determined.

The motor drive unit 1135 is connected to the instruction generation unit 111 for generating the position instruction and the speed instruction (a relationship between the instruction generation unit 111 and the position instruction as well as the speed instruction is not illustrated) in a manner capable of transmitting and receiving signals. Accordingly, the position instruction and the speed instruction are input from the instruction generation unit 111 to the motor drive unit 1135. In addition, the motor drive unit 1135 is electrically connected to the Y-axis direction tilt motor 135*a*. Further, the motor drive unit 1135 is connected to the first rotation information detection sensor 135*a*-1 in a manner capable of transmitting and receiving signals.

Accordingly, the motor drive unit 1135 can control the Y-axis direction tilt motor 135*a* on the basis of the speed instruction and/or position instruction and the amount of rotation of the Y-axis direction tilt motor 135*a*. Details of the motor drive unit 1135 will be described later.

Figure 7B:
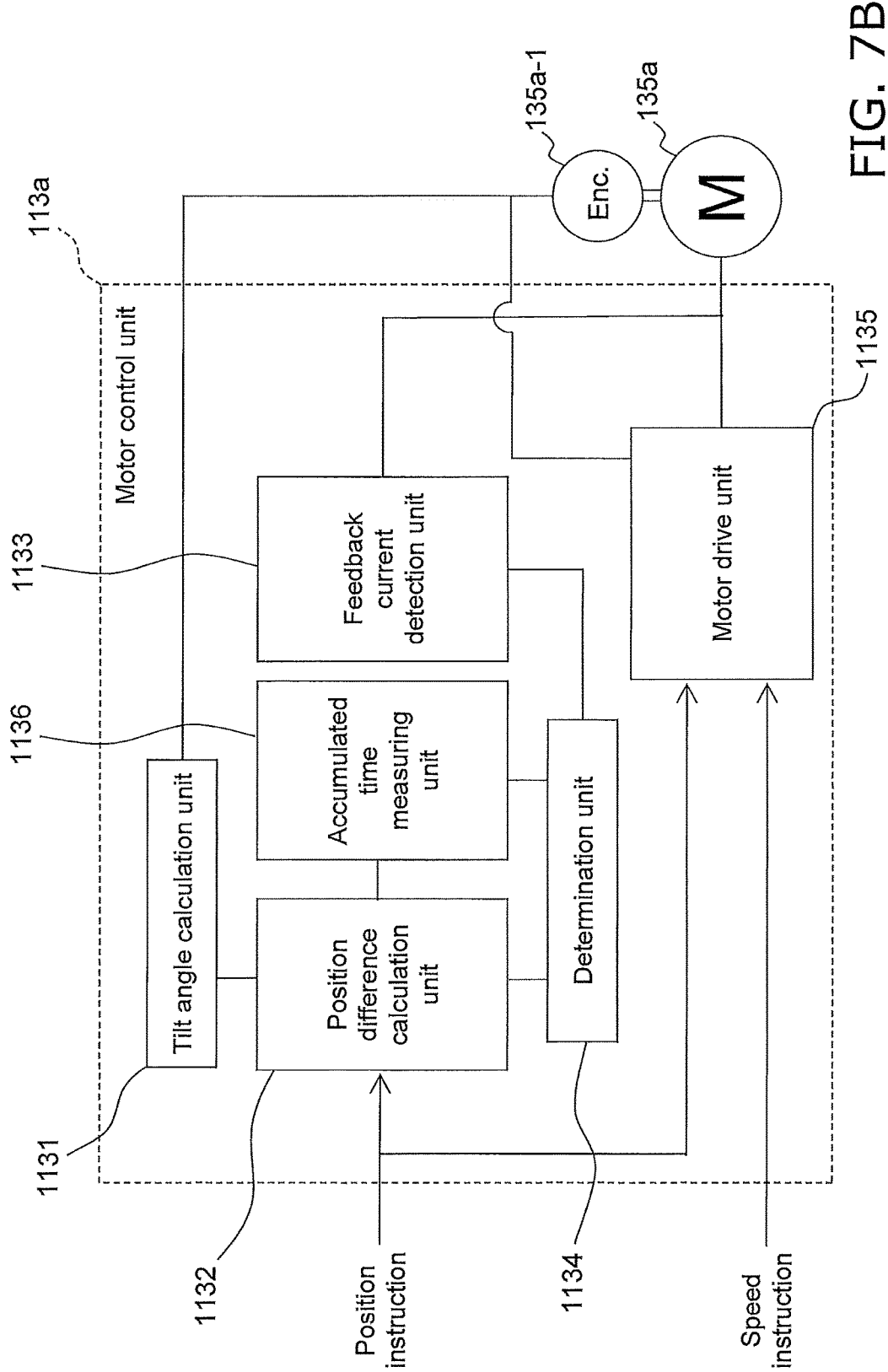
FIG. 7B is a diagram illustrating a structure of the motor control unit including an accumulated time measuring unit.

The motor control unit 113a may further include an accumulated time measuring unit 1136 as a first variation illustrated in FIG. 7B. The accumulated time measuring unit 1136 is connected to the position difference calculation unit 1132 in a manner capable of transmitting and receiving signals. The accumulated time measuring unit 1136 measures a time period during which the position difference per the first time period $T_1$ calculated by the position difference calculation unit 1132 is a second threshold $\varphi_2$ (described later) or higher and lower than the first threshold $\varphi_1$ (accumulated time $t_A$).

In addition, the accumulated time measuring unit 1136 is connected to the determination unit 1134 in a manner capable of transmitting and receiving signals. In this way, the accumulated time measuring unit 1136 can output the measured accumulated time $t_A$ to the determination unit 1134.

In the first variation in which the motor control unit 113a includes the accumulated time measuring unit 1136, the determination unit 1134 determines an error if the accumulated time $t_A$ is a third time period $T_3$ (described later) or longer. In this way, the training can be continued until the third time period $T_3$ elapses with respect to a position difference per the first time period $T_1$ having a value lower than the first threshold $\varphi_1$, i.e., with respect to a slowly changing position difference.

In addition, the determination unit 1134 can predict a load necessary for the Y-axis direction tilt motor 135a to move the training rod 3 from the slow position difference change. Accordingly, even if the feedback current value cannot be detected, the accumulated time measuring unit 1136 can measure the time period during which the slow position difference change continued, so as to measure the time period during which a load of predetermined value or more is applied to the Y-axis direction tilt motor 135a.

Figure 7C:
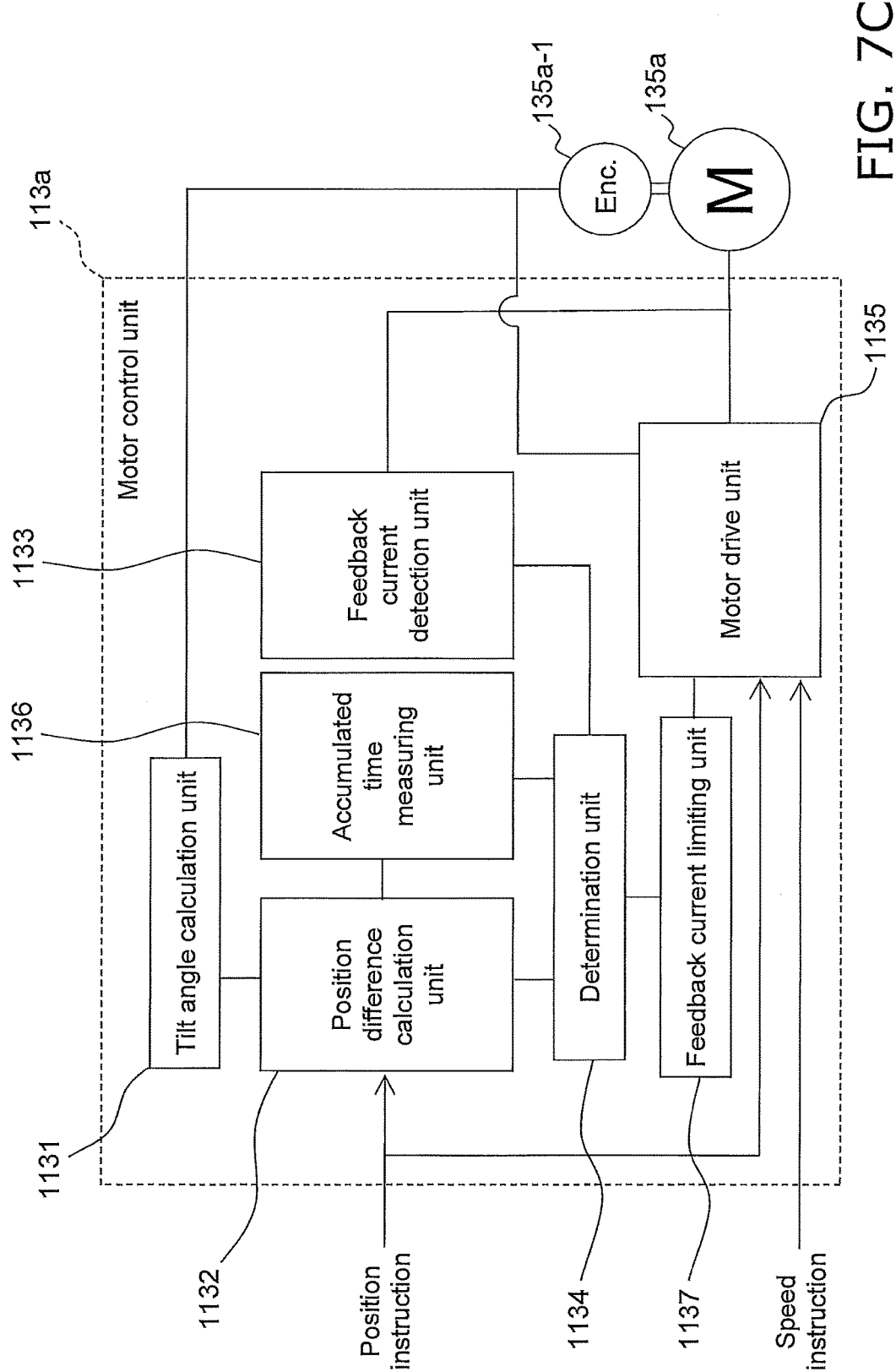
FIG. 7C is a diagram illustrating a structure of the motor control unit including the accumulated time measuring unit and a feedback current limiting unit.

The motor control unit 113a may include a feedback current limiting unit 1137 as a second variation illustrated in FIG. 7C. The feedback current limiting unit 1137 is connected to the determination unit 1134 and the motor drive unit 1135 in a manner capable of transmitting and receiving signals. The feedback current limiting unit 1137 limits the feedback current value output from the motor drive unit 1135 when the determination unit 1134 determines an error. When the feedback current limiting unit 1137 limits the feedback current value, the motor drive unit 1135 outputs the feedback current I having a second current value $I_2$ that is smaller than a rated current $I_R$ of the Y-axis direction tilt motor 135a, namely the second current value $I_2$ is calculated by multiplying the rated current $I_R$ by a predetermined number "a" smaller than one ($a \times I_R$).

III. Structure of Motor Drive Unit

Next, a structure of the motor drive unit 1135 is described with reference to FIG. 8. FIG. 8 is a diagram illustrating a structure of the motor drive unit 1135. The motor drive unit 1135 includes the speed control unit 1135-1, the position control unit 1135-2, a speed calculation unit 1135-3, the power supply unit 1135-4, a current limiting unit 1135-5, a first difference calculation unit 1135-6a, a second difference calculation unit 1135-6b, the combining unit 1135-7, a switching unit 1135-8, and a position difference setting unit 1135-9.

The speed control unit 1135-1 is connected to the second difference calculation unit 1135-6b in a manner capable of transmitting and receiving signals. Accordingly, the speed control unit 1135-1 receives a difference (a speed difference) between the speed instructed by the speed instruction (an instructed speed) and an actual speed of the Y-axis direction tilt motor 135a, which is calculated by the second difference calculation unit 1135-6b.

The speed control unit 1135-1 calculates the first control amount for controlling the power supply unit 1135-4 on the basis of the received speed difference. In this case, the speed control unit 1135-1 calculates the first control amount so as to eliminate the received speed difference. In other words, the speed control unit 1135-1 calculates the first control amount such that the actual motor speed follows the instructed speed.

As the speed control unit 1135-1, it is possible to use a control device that calculates a control amount such as to eliminate the speed difference on the basis of a control theory, for example. As this control device, there is a control device using a proportional integral derivative (PID) control theory, for example. In this embodiment, a control device using a proportional integral (PI) control theory is used as the speed control unit 1135-1.

When the speed control unit 1135-1 is the control device using the PI control theory, the first control amount is expressed as $K_{pv} \times \Delta v + K_{iv} \times Int(\Delta v)$, where $\Delta v$ represents the speed difference, $Int(\Delta v)$ represents an integrated value over time of the speed difference $\Delta v$, and $K_{pv}$ and $K_{iv}$ are constants called control gains.

The position control unit 1135-2 is connected to the first difference calculation unit 1135-6a in a manner capable of transmitting and receiving signals. Accordingly, the position control unit 1135-2 is supplied with a difference (position difference) between the tilt angle instructed by the position instruction (instructed tilt angle) and the actual tilt angle of the training rod 3, which is calculated by the first difference calculation unit 1135-6a. In addition, the position control unit 1135-2 calculates the second control amount for controlling the power supply unit 1135-4 on the basis of the position difference. In other words, the position control unit 1135-2 calculates the second control amount such that the actual tilt angle of the training rod 3 follows the instructed tilt angle (such as to eliminate the position difference).

As the position control unit 1135-2, similarly to the speed control unit 1135-1, a control device that performs control based on a control theory can be used. In this embodiment, a control device using the PI control theory is used as the position control unit 1135-2.

In this case, the second control amount is expressed as $K_{pp} \times \Delta\theta + K_{ip} \times Int(\Delta\theta)$, where $\Delta\theta$ represents the position difference, $Int(\Delta\theta)$ represents an integrated value over time of the position difference $\Delta\theta$, and $K_{pp}$ and $K_{ip}$ are constants called control gains.

The speed calculation unit 1135-3 is connected to the first rotation information detection sensor 135a-1 in a manner capable of transmitting and receiving signals. In this way, the speed calculation unit 1135-3 calculates the rotation speed of the Y-axis direction tilt motor 135a from the pulse signal output from the first rotation information detection sensor 135a-1. Note that the rotation speed of the Y-axis direction tilt motor 135a can be calculated from the number of pulses per unit time in the pulse signal.

The power supply unit 1135-4 is connected to the speed control unit 1135-1 via the combining unit 1135-7. In addition, the power supply unit 1135-4 is connected to the position control unit 1135-2 via the combining unit 1135-7 and the switching unit 1135-8.

In this way, only the first control amount output from the speed control unit 1135-1 is input to the power supply unit 1135-4, or the first control amount and the second control amount output from the position control unit 1135-2 are combined by the combining unit 1135-7 and input to the power supply unit 1135-4.

When only the first control amount is input to the power supply unit 1135-4, the power supply unit 1135-4 outputs the feedback current I on the basis of only the first control amount such that the speed (rotation speed) of the Y-axis direction tilt motor 135a follows the instructed speed. In this way, the motor drive unit 1135 can drive the Y-axis direction tilt motor 135a so that the rotation speed of the motor follows the instructed speed.

On the other hand, when the first control amount and the second control amount are combined by the combining unit 1135-7 and input to the power supply unit 1135-4, the power supply unit 1135-4 outputs the feedback current I such that the rotation speed of the motor follows the instructed speed and that the tilt angle of the training rod 3 follows the instructed tilt angle. In this way, the motor drive unit 1135 can drive the Y-axis direction tilt motor 135a not only so that the rotation speed of the motor follows the instructed speed but also that the tilt angle of the training rod 3 follows the instructed tilt angle.

Further, in this embodiment, the power supply unit 1135-4 outputs the current (feedback current I) controlled based on the first control amount and/or second control amount. However, output from the power supply unit 1135-4 is not limited to the feedback current. For instance, the power supply unit 1135-4 may output a voltage whose voltage value and/or duty ratio are controlled on the basis of the first control amount and/or second control amount.

The current limiting unit 1135-5 is electrically connected to the output of the power supply unit 1135-4 and the Y-axis direction tilt motor 135a. In addition, the current limiting unit 1135-5 is connected to the feedback current limiting unit 1137 in a manner capable of transmitting and receiving signals. Accordingly, when the current limiting unit 1135-5 receives the instruction to limit the feedback current I from the feedback current limiting unit 1137, the current limiting unit 1135-5 limits the feedback current value so that the feedback current value output from the power supply unit 1135-4 does not become the preset second current value $I_2$ or larger.

In this case, the current value, which is calculated by multiplying the rated current $I_R$ of the Y-axis direction tilt motor 135a by the predetermined number "a" smaller than one ($a \times I_R$), is set as the second current value $I_2$ in the current limiting unit 1135-5. In this way, when the determination unit 1134 determines an error, the feedback current I input to the Y-axis direction tilt motor 135a can be limited to the rated current value or smaller.

Each of the first difference calculation unit 1135-6a and the second difference calculation unit 1135-6b has two inputs (an input denoted by "+" and an input denoted by "−"). The input denoted by "+" of each of the first difference calculation unit 1135-6a and the second difference calculation unit 1135-6b is connected to the instruction generation unit 111 in a manner capable of transmitting and receiving signals. Further, the input denoted by "+" of the first difference calculation unit 1135-6a receives the position instruction from the instruction generation unit 111, while the input denoted by "+" of the second difference calculation unit 1135-6b receives the speed instruction from the instruction generation unit 111.

In addition, the input denoted by "−" of the first difference calculation unit 1135-6a is connected to the first rotation information detection sensor 135a-1 in a manner capable of transmitting and receiving signals. In this way, the input denoted by "−" of the first difference calculation unit 1135-6a receives the pulse signal output in accordance with the amount of rotation of the Y-axis direction tilt motor 135a calculated by the speed calculation unit 1135-3. Further, the input denoted by "−" of the second difference calculation unit 1135-6b is connected to the output of the speed calculation unit 1135-3 in a manner capable of transmitting and receiving signals. In this way, the input denoted by "−" of the second difference calculation unit 1135-6b receives the rotation speed of the Y-axis direction tilt motor 135a.

Accordingly, the first difference calculation unit 1135-6a calculates the position difference, i.e., the difference between the instructed tilt angle instructed by the position instruction and the actual tilt angle of the training rod 3. On the other hand, the second difference calculation unit 1135-6b calculates the speed difference, i.e., the difference between the instructed speed instructed by the speed instruction and the rotation speed of the Y-axis direction tilt motor 135a.

The combining unit 1135-7 combines the first control amount output from the speed control unit 1135-1 and the second control amount output from the position control unit 1135-2 (the combined control amount) and outputs the result to the power supply unit 1135-4. Here, the combined control amount is a control amount obtained by adding the first control amount and the second control amount after appropriate weighting. By appropriately adjusting the weighting on the first control amount and the weighting on the second control amount, it is possible to adjust whether to put importance on the control so that the rotation speed of the Y-axis direction tilt motor 135a follows the instructed speed (speed control) or on the control so that the tilt angle of the training rod 3 follows the instructed tilt angle (position control).

The switching unit 1135-8 is connected to the output of the position control unit 1135-2 and an input of the combining unit 1135-7. In addition, the switching unit 1135-8 is connected to the instruction generation unit 111 and the first rotation information detection sensor 135a-1 in a manner capable of transmitting and receiving signals. In this way, the switching unit 1135-8 turns on the switch of the switching unit 1135-8 when the number of pulses output from the first rotation information detection sensor 135a-1 (i.e., the actual tilt angle of the training rod 3) becomes a value corresponding to the deceleration start position instructed by the speed instruction. In other words, the switching unit 1135-8 enables the second control amount as the output from the position control unit 1135-2 to be received by the combining unit 1135-7 when the amount of rotation of the Y-axis direction tilt motor 135a becomes the value corresponding to the deceleration start position instructed by the speed instruction.

In this way, the switching unit 1135-8 can reflect the second control amount output from the position control unit 1135-2 on the control of the Y-axis direction tilt motor 135a only when the speed instruction is the deceleration instruction. As a result, the training rod 3 can reach the target tilt angle with a difference as small as possible when the deceleration instruction is executed.

The position difference setting unit 1135-9 is connected to the output of the first difference calculation unit 1135-6a and the input of the position control unit 1135-2 in a manner capable of transmitting and receiving signals. In addition, the position difference setting unit 1135-9 is connected to the instruction generation unit 111 and the first rotation information detection sensor 135a-1 in a manner capable of transmitting and receiving signals. In this way, the position difference setting unit 1135-9 sets the position difference output from the first difference calculation unit 1135-6a to zero (resets the same) when the number of pulses output from the first rotation information detection sensor 135a-1 becomes a value corresponding to the deceleration start position. By setting the (accumulated) position difference to zero (resetting the same) when decelerating the rotation speed of the Y-axis direction tilt motor 135a, it is possible to prevent the rotation speed of the motor from excessively increasing for correcting the position difference due to a temporary increase of the position difference when the motor is decelerated.

(5) Operation of Training Apparatus

I. Basic Operation of Training Apparatus

Figure 9:
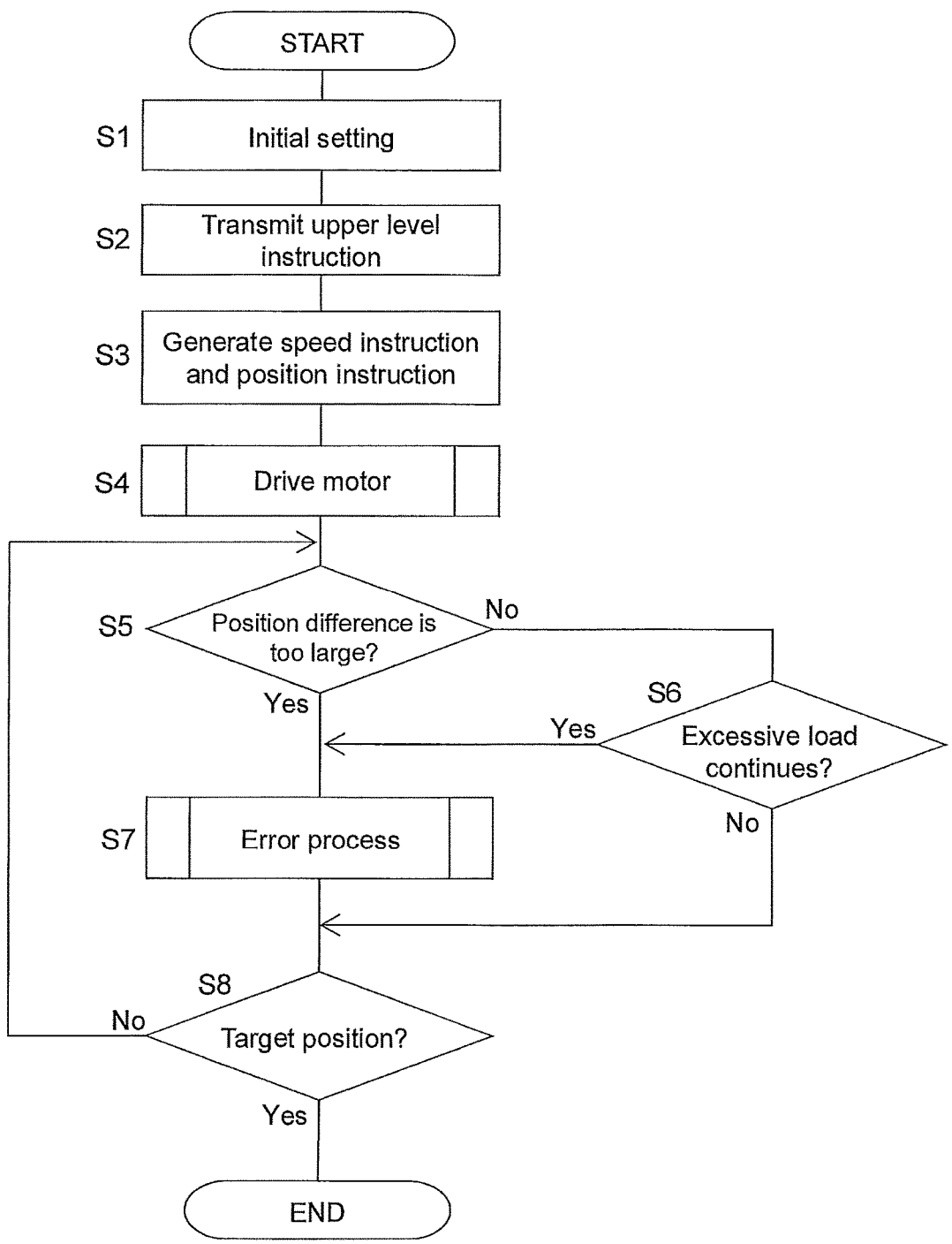
FIG. 9 is a flowchart illustrating a basic operation of the training apparatus.

Next, an operation of the training apparatus 100 is described. First, a basic operation of the training apparatus 100 is described with reference to FIG. 9. FIG. 9 is a flowchart illustrating a basic operation of the training apparatus 100. Further, in the following description, an operation of the training apparatus 100 when the training mode is set to the guided mode is exemplified for describing the operation of the training apparatus 100. In addition, in the example described below, it is supposed that the motor control unit 113a includes the accumulated time measuring unit 1136 and the feedback current limiting unit 1137 as illustrated in FIG. 7C. In addition, an operation of controlling the Y-axis direction tilt motor 135a by the motor control unit 113a is exemplified for describing the operation of the training apparatus 100. It is because the same control is performed also when the X-axis direction tilt motor 135b and the expansion/contraction motor 359 are controlled by the motor control units 113b and 113c, respectively.

First, the user makes various initial settings of the training apparatus 100 by using the training instruction unit 5 or the like (Step S1). In this case, the user of the training apparatus 100 sets the training mode to the guided mode by using the training instruction unit 5. Further, the user of the training apparatus 100 sets the training program of the limb of the patient in the guided mode by using the training instruction unit 5.

Next, the training instruction unit 5 generates the training rod operation instruction on the basis of the set training program. Further, the training instruction unit 5 transmits the training rod operation instruction (upper level instruction) to the instruction generation unit 111 of the control unit 11 (Step S2).

After that, the instruction generation unit 111, which has received the training rod operation instruction, generates the speed instruction and the position instruction on the basis of the target position information, the target speed information, and the acceleration rate information included in the training rod operation instruction (Step S3).

After the instruction generation unit 111 generates the speed instruction and the position instruction, the motor control unit 113a controls the Y-axis direction tilt motor 135a on the basis of the speed instruction and/or the position instruction (Step S4). Details of the drive of the Y-axis direction tilt motor 135a by the motor control unit 113a in this embodiment will be described later.

After the motor control unit 113a starts the drive of the Y-axis direction tilt motor 135a, the determination unit 1134 first determines whether or not the difference (position difference) between the instructed tilt angle instructed by the position instruction and the actual tilt angle of the training rod 3 is the first threshold $\varphi_1$ or higher (Step S5). In other words, in Step S5, it is determined whether or not the position difference per unit time (first time period $T_1$) becomes excessively large (position difference excessiveness).

If the position difference per the first time period $T_1$ is the first threshold $\varphi_1$ or higher ("Yes" in Step S5), the process proceeds to Step S7. On the other hand, if the position difference per the first time period $T_1$ is lower than the first threshold $\varphi_1$ ("No" in Step S5), the process proceeds to Step S6.

A method of determining the position difference excessiveness in Step S5 will be described later in detail.

In Step S6, the determination unit 1134 determines whether or not an excessive load (overload) has been applied on the limb continuously for a predetermined time period (the second time period $T_2$) in order that the Y-axis direction tilt motor 135a moves the limb of the patient. If the Y-axis direction tilt motor 135a applies an excessive load on the limb continuously for the second time period $T_2$ or longer ("Yes" in Step S6), the process proceeds to Step S7. On the other hand, if the time period during which the Y-axis direction tilt motor 135a applies an excessive load on the limb is shorter than the second time period $T_2$, or if the Y-axis direction tilt motor 135a does not apply an excessive load on the limb ("No" in Step S6), the process proceeds to Step S8.

If it is determined in Step S5 that the position difference is the first threshold $\varphi_1$ or higher, or if it is determined in Step S6 that an excessive load is applied on the limb for the second time period $T_2$ or longer, the determination unit 1134 determines an error (Step S7).

Note that when the determination unit 1134 determines an error, the training apparatus 100 performs various error processes.

As the error process in Step S7, the determination unit 1134 may inform the feedback current limiting unit 1137 of the error if the motor control unit 113a includes the feedback current limiting unit 1137. In addition, the feedback current limiting unit 1137, which has received the error, may drive the current limiting unit 1135-5 of the motor drive unit 1135. In this way, if the determination unit 1134 determines an error, the current value of the feedback current I input to the Y-axis direction tilt motor 135a is limited to the second current value $I_2$ smaller than the rated current $I_R$ ($a \times I_R$ ("a" is a positive number smaller than one)).

In general, a torque of a motor becomes larger as a value of the current supplied to a coil (winding) of a rotor and/or stator becomes larger. Accordingly, when the determination unit 1134 determines an error, the feedback current I supplied to the Y-axis direction tilt motor 135a is limited to the second current value $I_2$, and hence the torque output from the Y-axis direction tilt motor 135a is limited. As a result, when an error occurs in the training apparatus 100, the training rod 3 can be controlled without applying an excessive load on the patient.

In addition, as the error process in Step S7, the training instruction unit 5 provides visual or auditory information notifying occurrence of an error. In this way, the user can know a status of the training apparatus 100, namely that an error has occurred in the training apparatus 100 and/or about a cause of the error or the like.

In Step S7, when using the training apparatus 100, other error processing may be performed as necessary.

After the error process finishes in Step S7, or if it is determined "No" in Step S5 and it is determined "No" in Step S6 (i.e., if the determination unit 1134 determines that the position difference is lower than the first threshold $\varphi_1$ and the time period during which the Y-axis direction tilt motor 135a applies an excessive load on the limb is shorter than the second time period $T_2$, and in further other words, if an error is not determined), the motor control unit 113a determines whether or not the training rod 3 has reached the target tilt angle that is a tilt angle to be finally reached by the training rod 3 (Step S8).

If the tilt angle of the training rod 3 is the target tilt angle ("Yes" in Step S8), the control of the Y-axis direction tilt motor 135a by the motor control unit 113a is finished.

On the other hand, if the tilt angle of the training rod 3 has not reached the target tilt angle ("No" in Step S8), the process returns to Step S5.

Further, it is possible to determine whether or not the training rod 3 has reached the target tilt angle on the basis of the number of pulses output from the first rotation information detection sensor 135a–1, or on the basis of whether or not the speed instruction and/or the position instruction are all executed.

II. Motor Control Method

Figure 10:
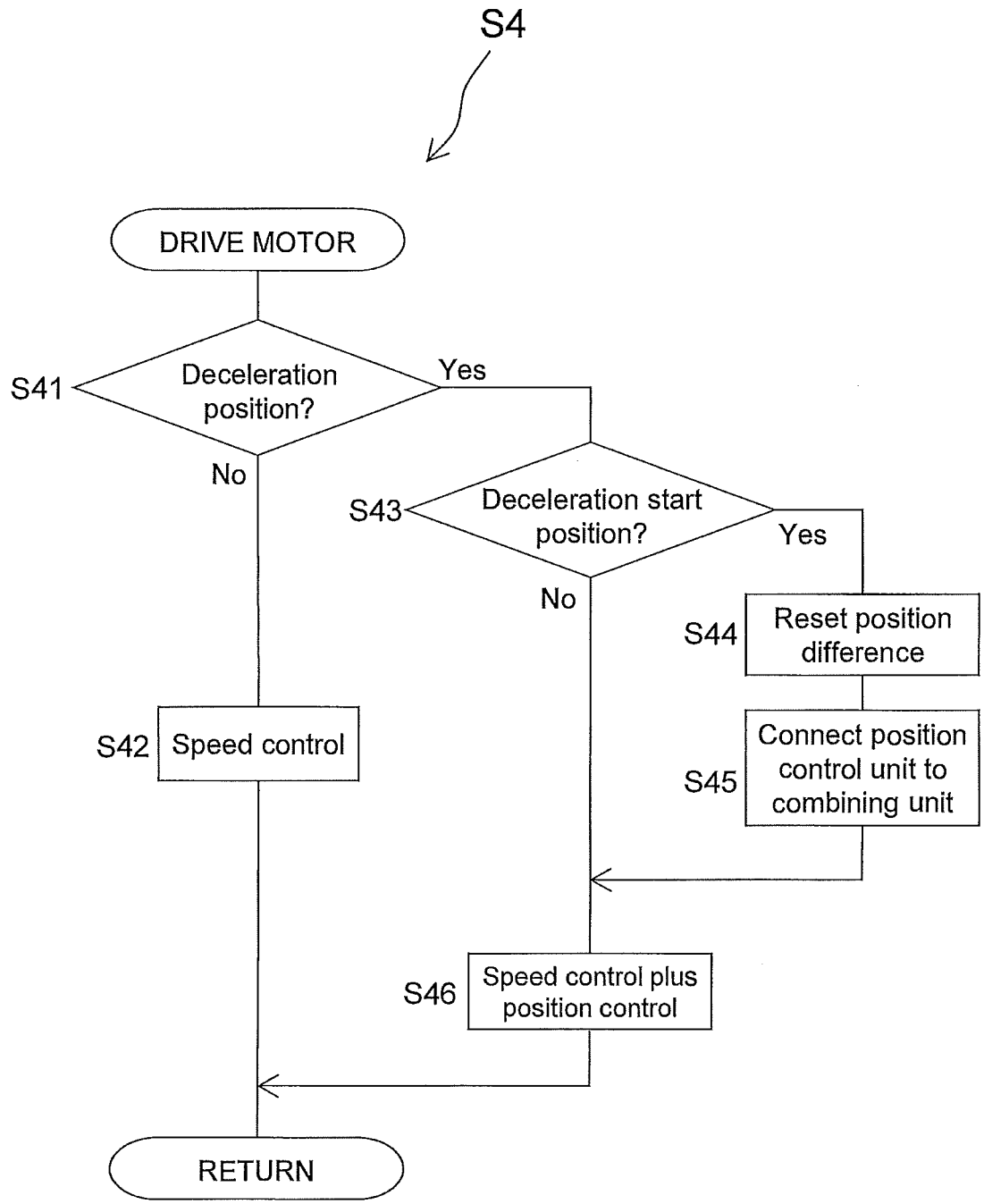
FIG. 10 is a flowchart illustrating a method of controlling a motor.

Next, the method of controlling the Y-axis direction tilt motor 135a in Step S4 is described with reference to FIG. 10. FIG. 10 is a flowchart illustrating the method of controlling the motor. In this embodiment, the motor control unit 113a controls the Y-axis direction tilt motor 135a to follow only the speed instruction when executing the acceleration instruction and/or the constant speed instruction of the speed instruction. Further, the motor control unit 113a controls the Y-axis direction tilt motor 135a to follow the speed instruction and the position instruction when executing the deceleration instruction.

When the motor drive is started, the switching unit 1135-8 first calculates the tilt angle of the training rod 3 from the number of pulses output from the first rotation information detection sensor 135a–1. Further, it is determined whether or not the calculated tilt angle of the training rod 3 is the tilt angle at which the deceleration instruction should be executed in the speed instruction (Step S41).

Figure 11:
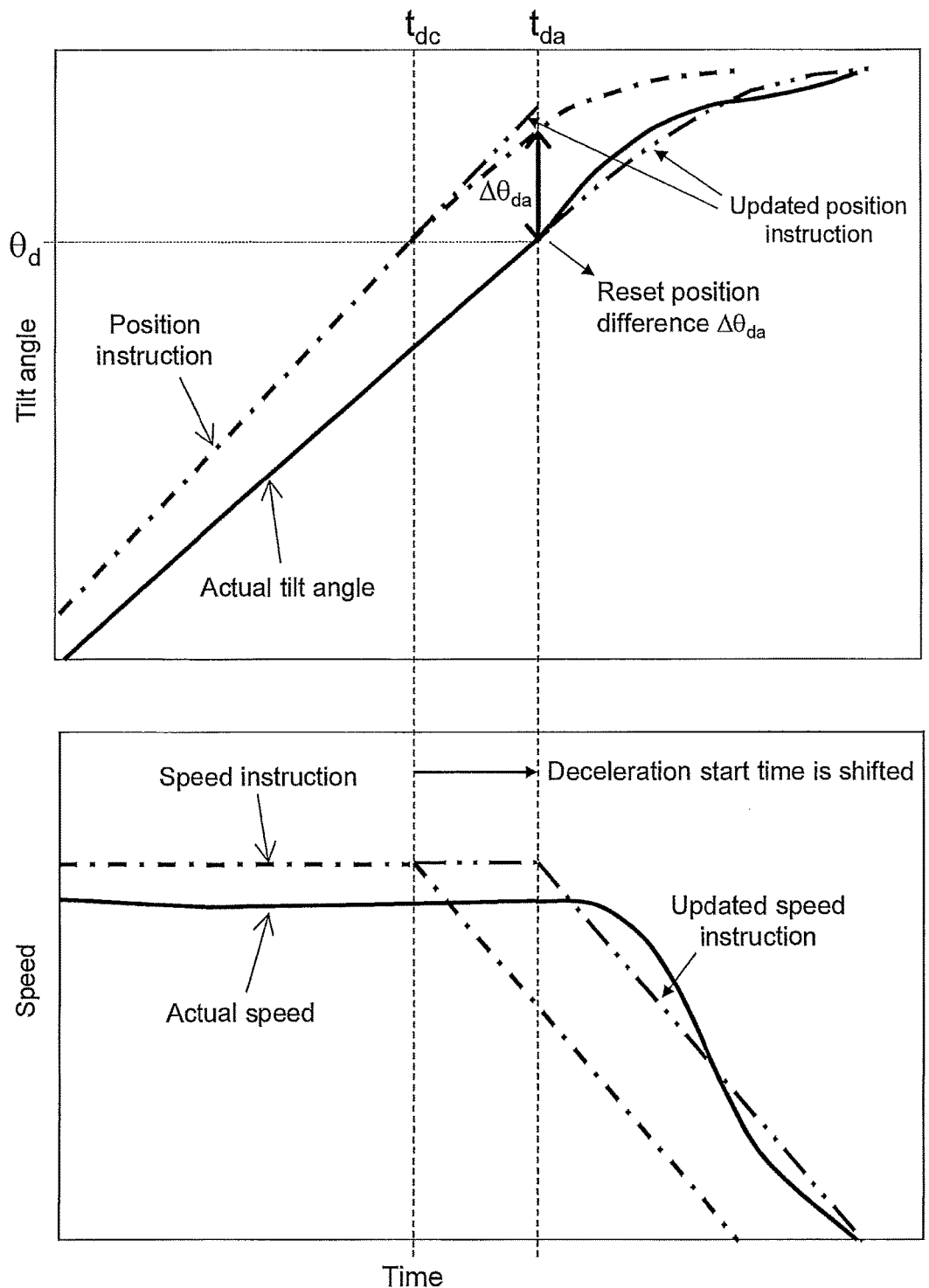
FIG. 11 is a graph schematically illustrating a manner of checking whether or not a tilt angle of the training rod is a tilt angle at which a deceleration instruction should be executed.

Here, with reference to FIG. 11, the operation in Step S41 is described in detail. FIG. 11 is a diagram schematically illustrating a manner of checking whether or not the tilt angle of the training rod 3 is the tilt angle at which the deceleration instruction should be executed.

In the position instruction and the speed instruction illustrated in FIG. 11 (both instructions are illustrated by a dot-dashed line in FIG. 11), the deceleration instruction is started when an elapsed time t from start of the drive of the Y-axis direction tilt motor 135a becomes $t_{dc}$. In this case, the instructed tilt angle of the training rod 3 at the elapsed time $t_{dc}$ is $\theta_d$. The instructed tilt angle $\theta_d$ corresponds to the deceleration start position. On the other hand, the actual tilt angle of the training rod 3 illustrated in FIG. 11 by a solid line is smaller than the instructed tilt angle $\theta_d$ (an example of the deceleration start position) also when the elapsed time is $t_{dc}$.

Accordingly, if the deceleration instruction is executed when the elapsed time from start of the drive of the Y-axis direction tilt motor 135a becomes $t_{dc}$, the control of the Y-axis direction tilt motor 135a may be stopped before the training rod 3 reaches the target tilt angle. Alternatively, when the deceleration instruction of the speed instruction is executed, the rotation speed of the Y-axis direction tilt motor 135a may be excessively increased in order to cancel the position difference. If the rotation speed of the Y-axis direction tilt motor 135a is excessively increased, an excessive load may be applied on the limb under training.

In order to solve the above-mentioned problem, in Step S4 (motor drive) of this embodiment, the execution of the deceleration instruction is started when the actual tilt angle of the training rod 3 becomes the tilt angle $\theta_d$ corresponding to the deceleration start position. As a result, in reality, the execution of the deceleration instruction is started when the elapsed time t from start of the motor drive becomes $t_{da}$ longer than $t_{dc}$.

In this way, the motor drive unit 1135 can control the Y-axis direction tilt motor 135a to accurately reach the target tilt angle while preventing the training rod 3 from applying an excessive load on the limb.

Specifically, if the actual tilt angle of the training rod 3 has not reached the tilt angle $\theta_d$ corresponding to the deceleration start position ("No" in Step S41), the process proceeds to Step S42. On the other hand, if the actual tilt angle of the training rod 3 is closer to the target tilt angle than the tilt angle $\theta_d$ corresponding to deceleration start position, i.e., if the actual tilt angle of the training rod 3 is a tilt angle at which the deceleration instruction should be executed in the speed instruction ("Yes" in Step S41), the process proceeds to Step S43.

In Step S41, if it is determined that the actual tilt angle of the training rod 3 has not reached the tilt angle $\theta_d$ corresponding to the deceleration start position, the switching unit 1135-8 electrically disconnects between the position control unit 1135-2 and the combining unit 1135-7 so that the second control amount output from the position control unit 1135-2 is not input to the combining unit 1135-7 (Step S42).

In this way, only the first control amount output from the speed control unit 1135-1 is reflected when the power supply unit 1135-4 outputs the feedback current. As a result, the motor drive unit 1135 controls the Y-axis direction tilt motor 135a so that the rotation speed of the Y-axis direction tilt motor 135a follows only the instructed speed (speed control).

Further, when the actual tilt angle of the training rod 3 is smaller than the tilt angle $\theta_d$ as the deceleration start position, the acceleration instruction or the constant speed instruction is executed in the speed instruction. Accordingly, when the acceleration instruction or the constant speed instruction is executed in the speed instruction, the motor drive unit 1135 controls the Y-axis direction tilt motor 135a so that the rotation speed of the Y-axis direction tilt motor 135a follows only the instructed speed.

Figure 12:
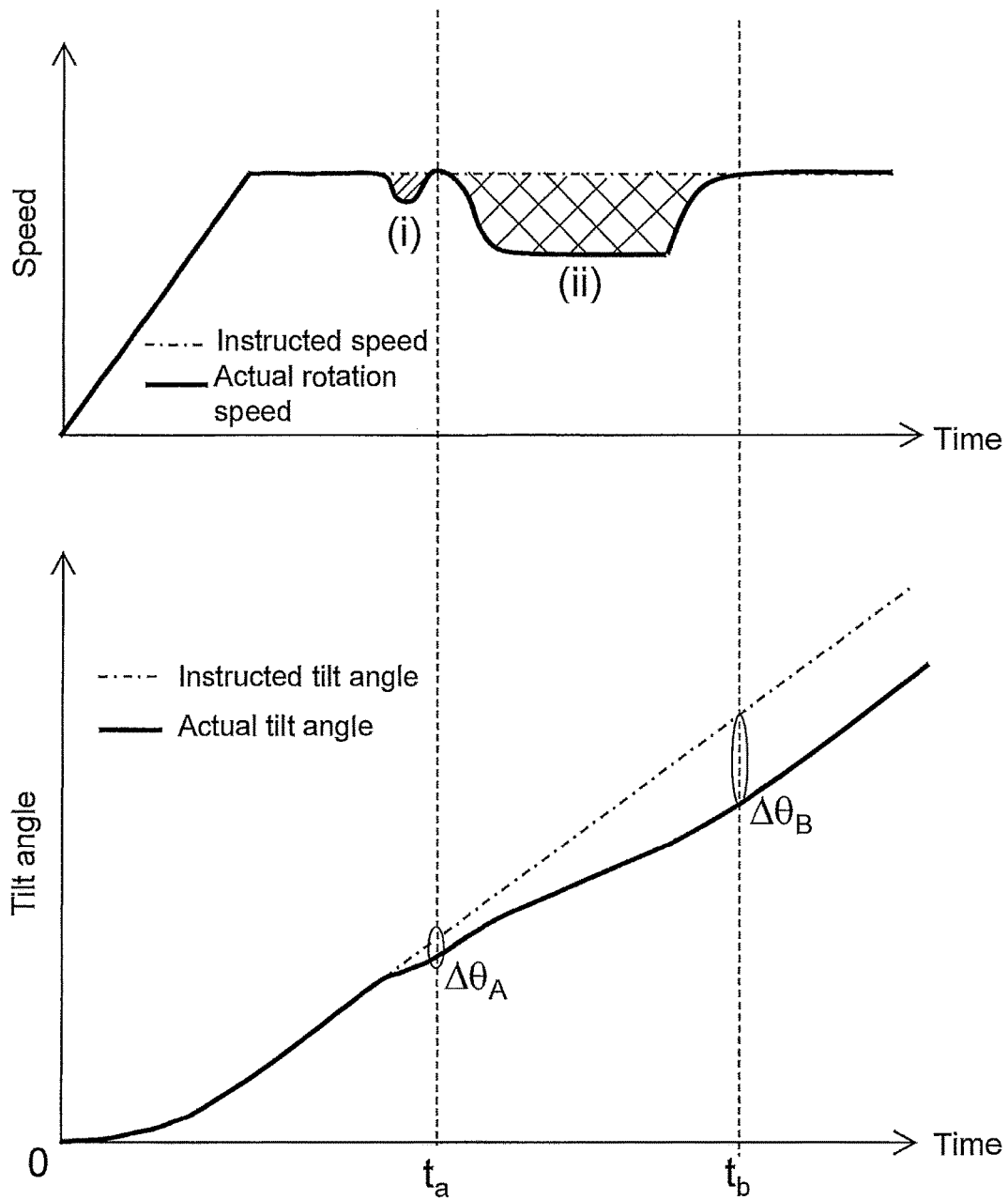
FIG. 12 is a graph schematically illustrating an accumulated and maintained position difference.

In addition, when the Y-axis direction tilt motor 135a is controlled only by the speed control, the position difference between the instructed tilt angle and the actual tilt angle of the training rod 3 generated due to the speed difference between the actual rotation speed of the Y-axis direction tilt motor 135a and the instructed speed is accumulated and maintained as illustrated in FIG. 12. For instance, at a time point $t_A$ when the speed difference (i) generated first in the example of FIG. 12 is canceled, a position difference $\Delta\theta_A$ corresponding to a time integration of the speed difference (i) (an area of the region illustrated by hatching in the graph) is maintained. After that, at a time point $t_b$ when the speed difference (ii) generated second is canceled, a position difference $\Delta\theta_B$ in which the position difference corresponding to a time integration of a speed difference (ii) (an area of the region illustrated by crosshatching in the graph) is further accumulated on the position difference $\Delta\theta_A$ is maintained. Further, after the time point $t_b$, even if the speed difference is canceled, the position difference $\Delta\theta_B$ is maintained without changing.

In this way, when the motor is controlled only by the speed control, the rotation speed of the Y-axis direction tilt motor 135a follows the instructed speed, while the position difference is not canceled but is accumulated and maintained. It is because the position difference is not considered in the speed control when the speed control unit 1135-1 calculates the first control amount.

It is preferred for the training apparatus 100 to continue the training even if the position difference occurs in some amount as long as the limb movement can follow the movement of the training rod 3 indicated in the training rod operation instruction in a certain degree. Accordingly, when the acceleration instruction and/or constant speed instruction of the speed instruction is executed, by controlling the Y-axis direction tilt motor 135a only by the speed control, the Y-axis direction tilt motor 135a can be controlled to follow the speed instruction without canceling the position difference. As a result, even if there is the position difference in some amount, the training of the limb can be continued while a moving speed of the training rod 3 follows the moving speed indicated in the training rod operation instruction.

If it is determined in Step S41 that the actual tilt angle of the training rod 3 is the tilt angle at which the deceleration instruction should be executed in the speed instruction ("Yes" in Step S41), the process proceeds to Step S43.

In Step S43, the position difference setting unit 1135-9 checks whether or not the actual tilt angle of the training rod 3 is the tilt angle $\theta_d$ corresponding to the deceleration start position. If the actual tilt angle of the training rod 3 is $\theta_d$ ("Yes" in Step S43), the process proceeds to Step S44. On the other hand, if the actual tilt angle of the training rod 3 is not $\theta_d$ ("No" in Step S43), the process proceeds to Step S46.

In Step S43, if it is determined that the actual tilt angle of the training rod 3 is $\theta_d$, the position difference setting unit 1135-9 first resets the accumulated and maintained position difference (sets the position difference to zero) in a period while the training rod 3 moves to the tilt angle $\theta_d$ (Step S44). In the example illustrated in FIG. 11, the accumulated and maintained position difference $\Delta\theta_{da}$ is set to zero at the elapsed time $t_{da}$ when the actual tilt angle becomes $\theta_d$.

The position difference $\Delta\theta_{da}$ at the elapsed time $t_{da}$ is reset, for example, by updating the position instruction so that the instructed tilt angle at the elapsed time $t_{da}$ becomes $\theta_d$ (the position instruction illustrated in FIG. 11 by a double-dot-dashed line). In addition, at the same time, the speed instruction is updated so that the deceleration instruction is started at the elapsed time $t_{da}$ (the speed instruction illustrated in FIG. 11 by a double-dot-dashed line).

After the position difference is reset in Step S44, the switching unit 1135-8 electrically connects the position control unit 1135-2 to the combining unit 1135-7 (Step S45). In other words, the second control amount output from the position control unit 1135-2 can be input to the combining unit 1135-7. In this way, when the deceleration instruction is executed, not only the first control amount but also the second control amount is reflected when the power supply unit 1135-4 outputs the feedback current I.

When the deceleration instruction of the speed instruction is executed, the position control is also performed in addition to the speed control. Accordingly, if the position difference is not reset at the deceleration start position, other information processing for canceling the accumulated and maintained position difference $\Delta\theta_{da}$ should be performed when the execution of the deceleration instruction is started. It is because if this processing is not performed, the rotation speed of the Y-axis direction tilt motor 135a may be increased to an excessive speed higher than the speed instruction by the accumulated and maintained position difference $\Delta\theta_{da}$ when the execution of the deceleration instruction is started. This is because if the position difference is not canceled by the information processing, a ratio of the second control amount in the combined control amount may be increased. In this way, despite that the deceleration instruction is being executed, if the rotation speed of the Y-axis direction tilt motor 135a is excessively increased, an excessive load is applied on the limb of the patient.

On the other hand, by resetting the position difference at the deceleration start position, even if the position control is performed when the deceleration instruction is executed, the rotation speed of the Y-axis direction tilt motor 135a can be prevented from being excessively increased. As a result, it is possible to continue the training without applying a large load on the limb of the patient from the training rod 3.

If the actual tilt angle of the training rod 3 is not $\theta_d$ ("No" in Step S43), or after resetting the position difference $\Delta\theta_{da}$ in Step S44, the motor drive unit 1135 drives the Y-axis direction tilt motor 135a so that the rotation speed of the Y-axis direction tilt motor 135a follows the instructed speed of the speed instruction and that the tilt angle of the training rod 3 follows the instructed tilt angle of the position instruction (Step S46). In this way, the motor drive unit 1135 controls the Y-axis direction tilt motor 135a so that the training rod 3 reaches the target tilt angle with a difference as small as possible.

III. Position Difference Excessiveness Determination Method

Figure 13:
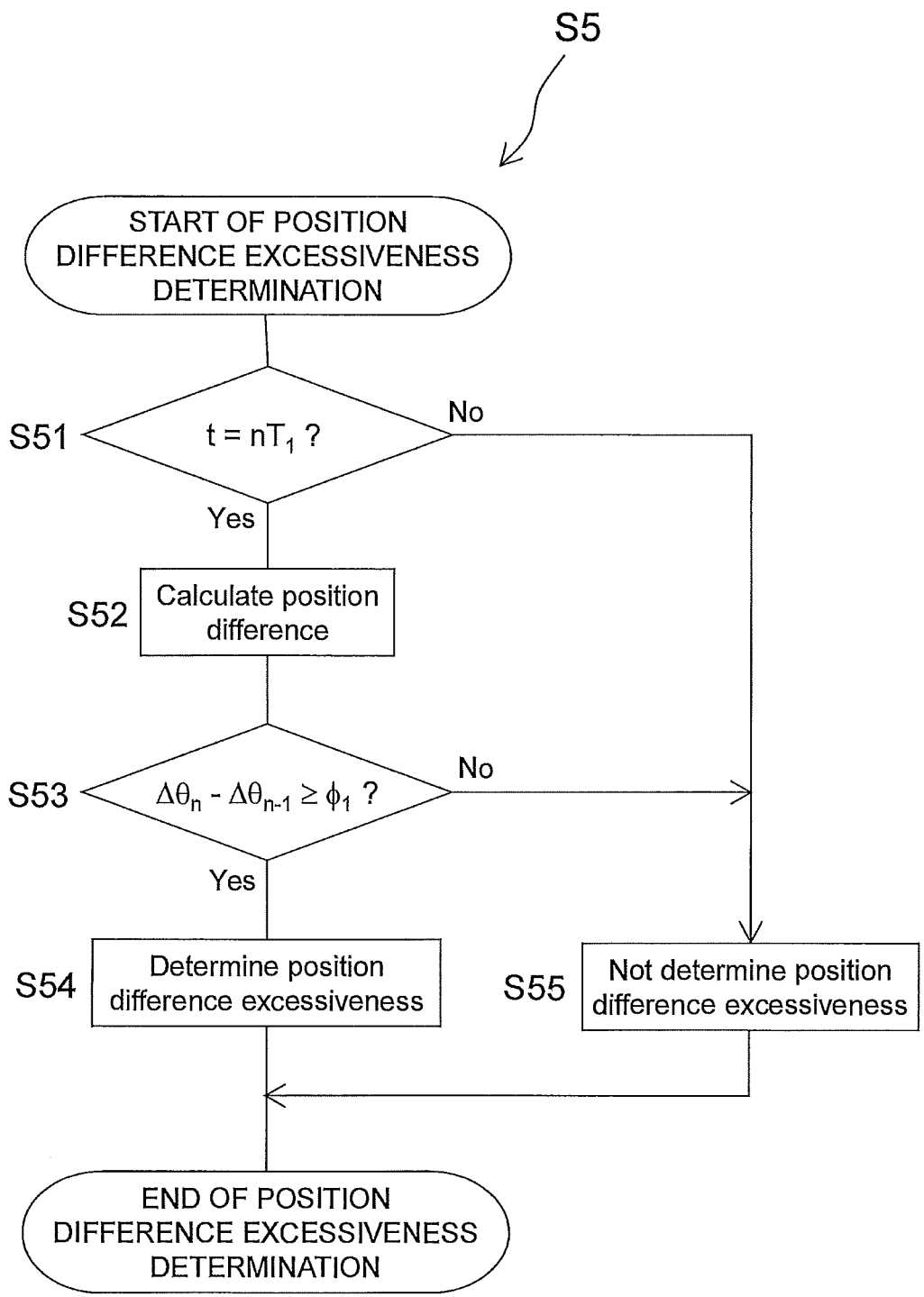
FIG. 13 is a flowchart illustrating a position difference excessiveness determination method.

Next, the position difference excessiveness determination method in Step S5 of the flowchart illustrated in FIG. 9 is described with reference to FIG. 13. FIG. 13 is a flowchart illustrating the position difference excessiveness determination method.

After starting the position difference excessiveness determination, the determination unit 1134 first determines whether or not the elapsed time t from start of the drive of the Y-axis direction tilt motor 135a is a multiple of the first time period $T_1$ and an integer (n) (Step S51). If the elapsed time t is not a multiple of the first time period $T_1$ and an integer ("No" in Step S51), the determination unit 1134 determines that the position difference excessiveness has not occurred (Step S55) and finishes the position difference excessiveness determination.

On the other hand, if the elapsed time t is a multiple of the first time period $T_1$ and an integer ("Yes" in Step SM), the determination unit 1134 instructs the position difference calculation unit 1132 to calculate the position difference that is currently accumulated and maintained (Step S52). Further, the determination unit 1134 regards the calculated position difference as a position difference $\Delta\theta_n$ accumulated and maintained at an elapsed time $t=nT_1$, and stores the same in a storage device of the motor control unit 113a or the like.

Next, the determination unit 1134 determines whether or not the position difference generated per the first time period $T_1$ is the first threshold $\varphi_1$ or higher (Step S53). Specifically, the determination unit 1134 first reads out a position difference $\Delta\theta_{n-1}$ calculated last time, namely, the position difference accumulated and maintained at an elapsed time $t=(n-1)T_1$ from the storage device of the motor control unit 113a or the like. Further, the determination unit 1134 calculates a difference $\Delta\theta_n-\Delta\theta_{n-1}$ between the position difference $\Delta\theta_n$ at the elapsed time $t=nT_1$ and the position difference $\Delta\theta_{n-1}$ at the elapsed time $t=(n-1)T_1$. In this way, the position difference generated per the first time period $T_1$ (i.e., per unit time)

at the elapsed time $t=nT_1$ is calculated. After that, the determination unit 1134 determines whether or not $\Delta\theta_n - \Delta\theta_{n-1}$ is the first threshold $\varphi_1$ or higher.

If $\Delta\theta_n - \Delta\theta_{n-1}$ is the first threshold $\varphi_1$ or higher ("Yes" in Step S53), the determination unit 1134 determines that the position difference excessiveness has occurred (Step S54) and finishes the position difference excessiveness determination. On the other hand, if $\Delta\theta_n - \Delta\theta_{n-1}$ is lower than the first threshold $\varphi_1$ ("No" in Step S53), the determination unit 1134 determines that the position difference excessiveness has not occurred (Step S55) and finishes the position difference excessiveness determination.

In this way, by calculating the difference between the position difference at a certain elapsed time and the position difference first time period $T_1$ before the elapsed time, the position difference generated per the first time period $T_1$ (per unit time) can be calculated. Further, by determining whether or not the position difference per the first time period $T_1$ is the first threshold $\varphi_1$ or higher, the determination unit 1134 can detect a rapid position difference change.

IV. Excessive Load Duration Detection Method

Next, there is described a method for the determination unit 1134 to determine whether or not the training rod 3 (the Y-axis direction tilt motor 135*a*) has applied an excessive load (overload) on the limb continuously for a predetermined time period (the second time period $T_2$) (excessive load duration detection method). As the excessive load duration detection method, there are (i) a method of detection using the feedback current value, and (ii) a method of detection using the position difference. Hereinafter, the method (i) and the method (ii) are respectively described.

(i) Excessive Load Duration Detection Method Using Feedback Current Value

Figure 14:
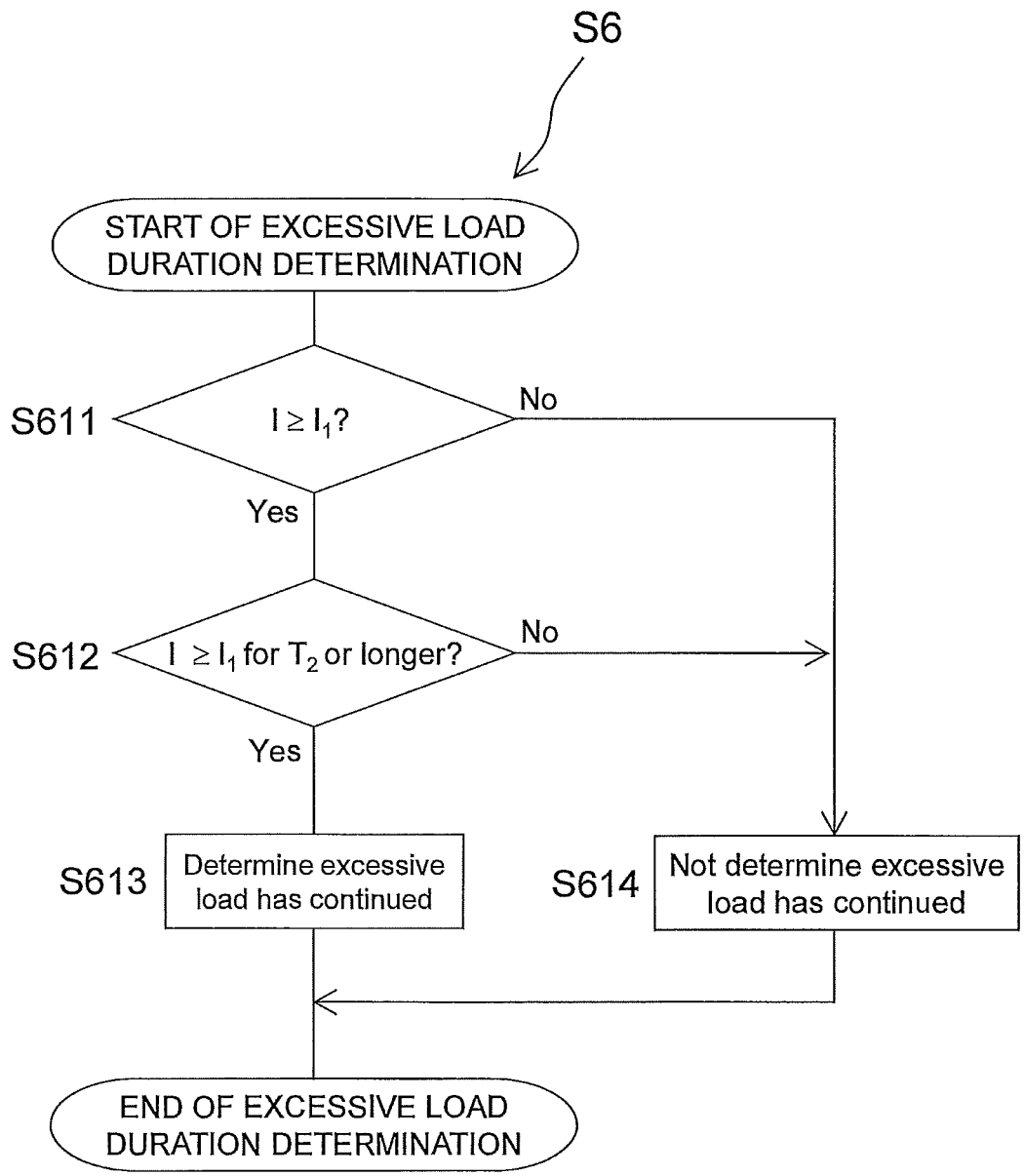
FIG. 14 is a flowchart illustrating an excessive load duration detection method using a feedback current value.

First, the excessive load duration detection method using the feedback current value is described with reference to FIG. 14. FIG. 14 is a flowchart illustrating an excessive load duration detection method using the feedback current value.

First, when the excessive load duration detection is started, the feedback current detection unit 1133 detects whether or not the feedback current I is the first current value $I_1$ or higher (Step S611). If the feedback current I is the first current value $I_1$ or higher ("Yes" in Step S611), the process proceeds to Step S612. On the other hand, if the feedback current I is smaller than the first current value $I_1$ ("No" in Step S611), the determination unit 1134 determines that the excessive load state has not continued (Step S614) and finishes the excessive load duration detection.

If it is determined in Step S611 that the feedback current I is the first current value $I_1$ or higher ("Yes" in Step S611), the determination unit 1134 determines whether or not that the state where the feedback current I is the first current value $I_1$ or higher has continued for the second time period $T_2$ or longer (Step S612). If the state where the feedback current I is the first current value I, or higher has continued for the second time period $T_2$ or longer ("Yes" in Step S612), the determination unit 1134 determines that the excessive load state has continued (Step S613) and finishes the excessive load duration detection.

On the other hand, if the continuation time in which the feedback current I is the first current value $I_1$ or higher is shorter than the second time period $T_2$ ("No" in Step S612), the determination unit 1134 determines that the excessive load state has not continued (Step S614) and finishes the excessive load duration detection.

Figure 15:
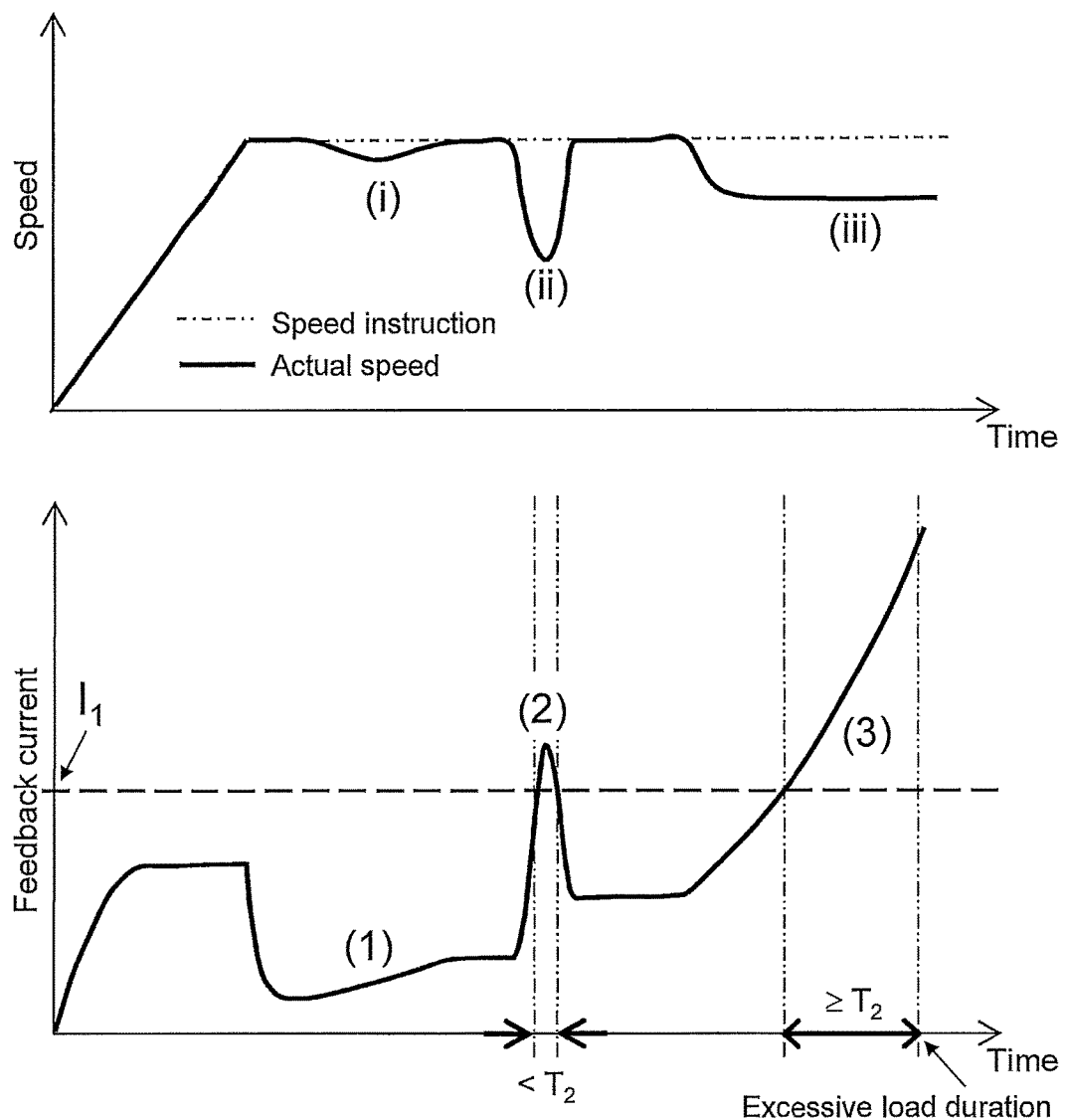
FIG. 15 is a graph schematically illustrating a relationship between an actual rotation speed of the motor and the speed instruction, and a temporal change of the feedback current due to occurrence of a speed difference.

Here, the excessive load duration detection using the feedback current value is further described with reference to FIG. 15. FIG. 15 is a graph schematically illustrating a relationship between an actual rotation speed of the motor and the speed instruction (the instructed speed), and a temporal change of the feedback current I due to occurrence of a speed difference. As illustrated in FIG. 15, when the constant speed instruction is executed, it is supposed that three rotation speed changes (speed change (i), speed change (ii), and speed change (iii)) have occurred in the Y-axis direction tilt motor 135*a*, for example. As described above, when the constant speed instruction is executed, the Y-axis direction tilt motor 135*a* is controlled to follow only the speed instruction.

The speed change such as (i) in FIG. 15 occurs, for example, in a case where the training apparatus 100 is operated in the guided mode, when a certain degree of auxiliary force is applied to the limb in the training via the training rod 3 so that the limb movement can follow the training program. The speed change such as (ii) in FIG. 15 occurs, for example, in a case where the limb movement is substantially stopped for a short period in the training but afterward the limb starts moving. The speed change such as (iii) in FIG. 15 occurs in a case where the limb movement cannot follow the training program even if the auxiliary force is applied to the limb in the training.

First, a feedback current value change when the speed change (i) in FIG. 15 occurs is described. At a certain elapsed time, a small speed difference (i) occurs for a reason that the limb in the training can hardly follow the training program. In this case, the speed control unit 1135-1 outputs a small first control amount corresponding to the small speed change. This is apparent also from the expression $K_{p,v} \times \Delta v + K_{i,v} \times \text{Int}(\Delta v)$ for calculating the first control amount as described above. If the first control amount is small, the feedback current I slowly increases ((1) in FIG. 15). It is because that the increase of the feedback current I is caused by accumulation of the first control amount. As the feedback current I increases, the torque output from the Y-axis direction tilt motor 135*a* also slowly increases. It is because the torque output from the motor changes in accordance with the feedback current I.

Further, when the torque output from the Y-axis direction tilt motor 135*a* increases to a certain extent so that the limb movement in the training can follow the training program, the speed difference is canceled. Further, when the speed difference is canceled, an increase of the feedback current I is stopped.

As illustrated in FIG. 15, the current value of the feedback current I after the speed difference (i) is canceled is the first current value I, or smaller. This means that the torque output from the Y-axis direction tilt motor 135*a* after the speed difference (i) is canceled is not so large as the torque (excessive load) that forces the limb to move in the training. In this case, the training of the limb can be continued.

In this way, when it is determined whether or not the feedback current I is the first current value $I_1$ or higher, it can be determined whether or not the Y-axis direction tilt motor 135*a* does not apply an excessive load on the limb via the training rod 3. Accordingly, if the current value of the feedback current I is smaller than the first current value $I_1$, the determination unit 1134 can determine that the excessive load state has not continued. As a result, if the current value of the feedback current I is smaller than the first current value $I_1$, it is determined that the Y-axis direction tilt motor 135*a* does not apply an excessive load on the limb, and the training apparatus 100 can continue the training program of the limb.

Note that the first current value $I_1$ is appropriately set on the basis of a standard for determining an excessive load.

Accordingly, the first current value $I_1$ may be adjustable based on a training level or the like.

On the other hand, if a large speed difference has occurred in a short period due to a stop of the limb movement for a short period (corresponding to the speed change (ii) in FIG. 15), the current value of the feedback current I becomes larger than the first current value $I_1$ ((2) in FIG. 15). However, the period while the current value of the feedback current I is larger than the first current value $I_1$ is shorter than the second time period $T_2$.

In this case, the limb cannot follow the training program temporarily, but the limb movement can follow the training program in a period other than the period while it cannot follow the training program. Also in this case, the training apparatus 100 can continue the training of the limb.

Accordingly, if the period while current value of the feedback current I is the first current value $I_1$ or higher is the second time period $T_2$ or shorter, the determination unit 1134 determines that the excessive load state has not continued and does not determine an error. As a result, the training apparatus 100 can continue the training program of the limb in the case where the Y-axis direction tilt motor 135a applies an excessive load on the limb only temporarily for a short period.

Note that the second time period $T_2$ is also set appropriately similarly to the first current value $I_1$ on the basis of a reference time for determining that an excessive load has continued. Accordingly, the second time period $T_2$ may also be adjustable in accordance with the training level or the like.

On the other hand, if the speed difference is not canceled for a long period (corresponding to the speed change (iii) in FIG. 15), the current value of the feedback current I continues to increase as long as the speed difference is not canceled ((3) in FIG. 15). In this case, the load applied on the limb continues to increase until the limb can follow the training program. In this way, if the limb cannot follow the training program even if any load is applied on the limb, it is preferred not to apply an excessive load on the limb.

Accordingly, if the state where the current value of the feedback current I is the first current value $I_1$ or higher continues for the second time period $T_2$ or longer, the determination unit 1134 determines that the excessive load state has continued and determines an error. Further, in this embodiment, when an error has occurred, the feedback current I is limited to the second current value $I_2$ ($a \times I_R$). As a result, if the Y-axis direction tilt motor 135a applies an excessive load on the limb for a long period, the feedback current I can be limited so that the Y-axis direction tilt motor 135a does not apply an excessive load on the limb. In addition, it is possible to prevent an excessive electric load from being applied on the control unit 11 of the training apparatus 100.

Figure 16:
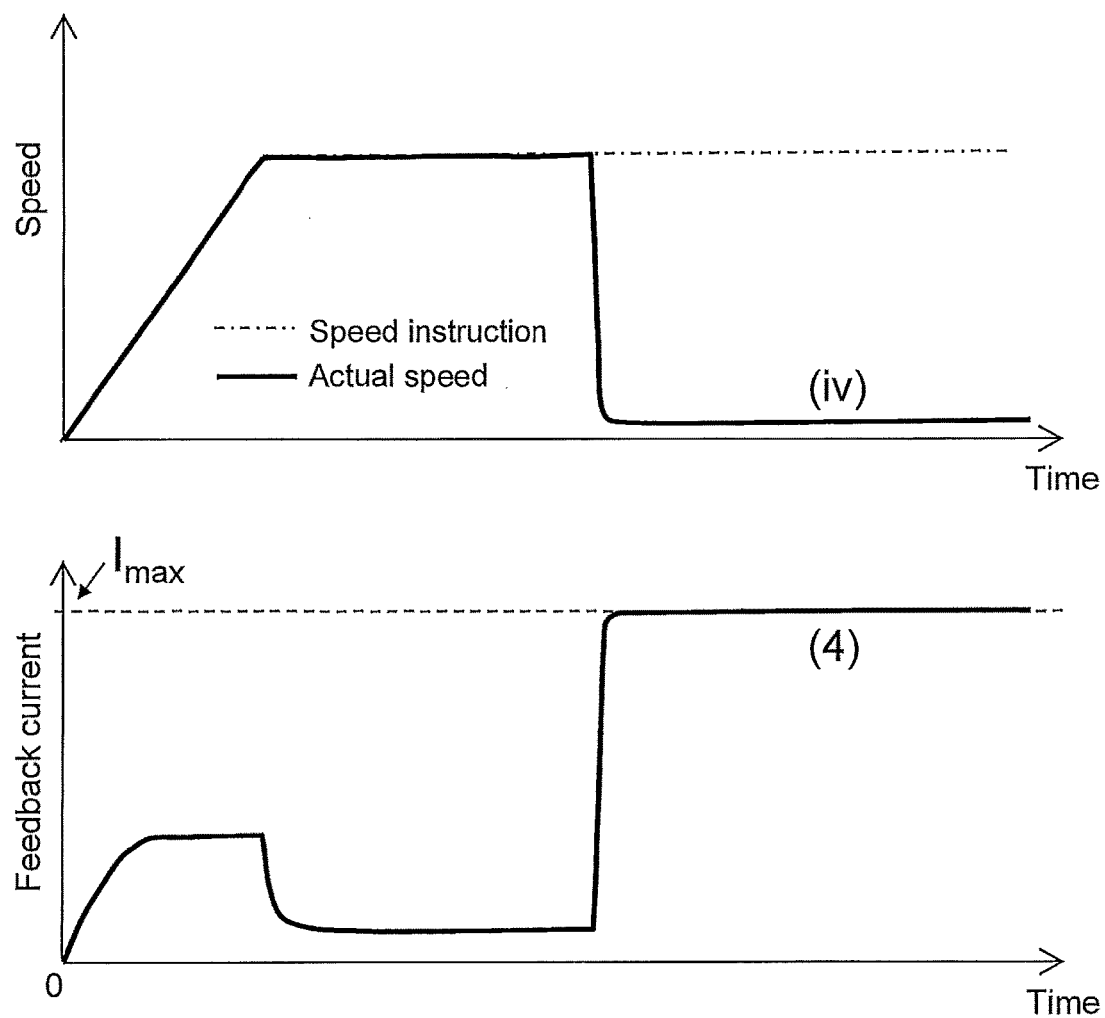
FIG. 16 is a graph illustrating a temporal change of the feedback current when a speed change with a large speed difference has occurred during a long period.

Here, the change of the current value of the feedback current I in the case where the speed change (i) to (iii) illustrated in FIG. 15 has occurred is compared with the change of the current value of the feedback current I in the case where the speed change (iv) with a large speed difference for a long period as illustrated in FIG. 16 has occurred. The speed change (iv) with a large speed difference for a long period as illustrated in FIG. 16 occurs, for example, in the case where the limb in the training is substantially unable to move.

When a speed change such as the speed change (iv) occurs, the feedback current I increases in a short period up to a maximum current $I_{max}$ that can be output to the Y-axis direction tilt motor 135a. Further, the feedback current I does not decrease from the maximum current $I_{max}$.

On the other hand, as illustrated in FIG. 15, in the change (1) to (3) of the feedback current I in which the speed change (i) to (iii) has occurred, the feedback current I increases relatively slowly (changes (1) and (3)) or becomes a current value above the first current value $I_1$ in a short period (change (2)). Accordingly, by monitoring the change of the feedback current I, it is possible to determine whether a speed change causing a large speed difference (a rapid change of the position difference), a speed change causing a small speed difference (a slow change of the position difference), or a large speed difference in a short period.

(ii) Excessive Load Duration Detection Method Using Position Difference

Figure 17:
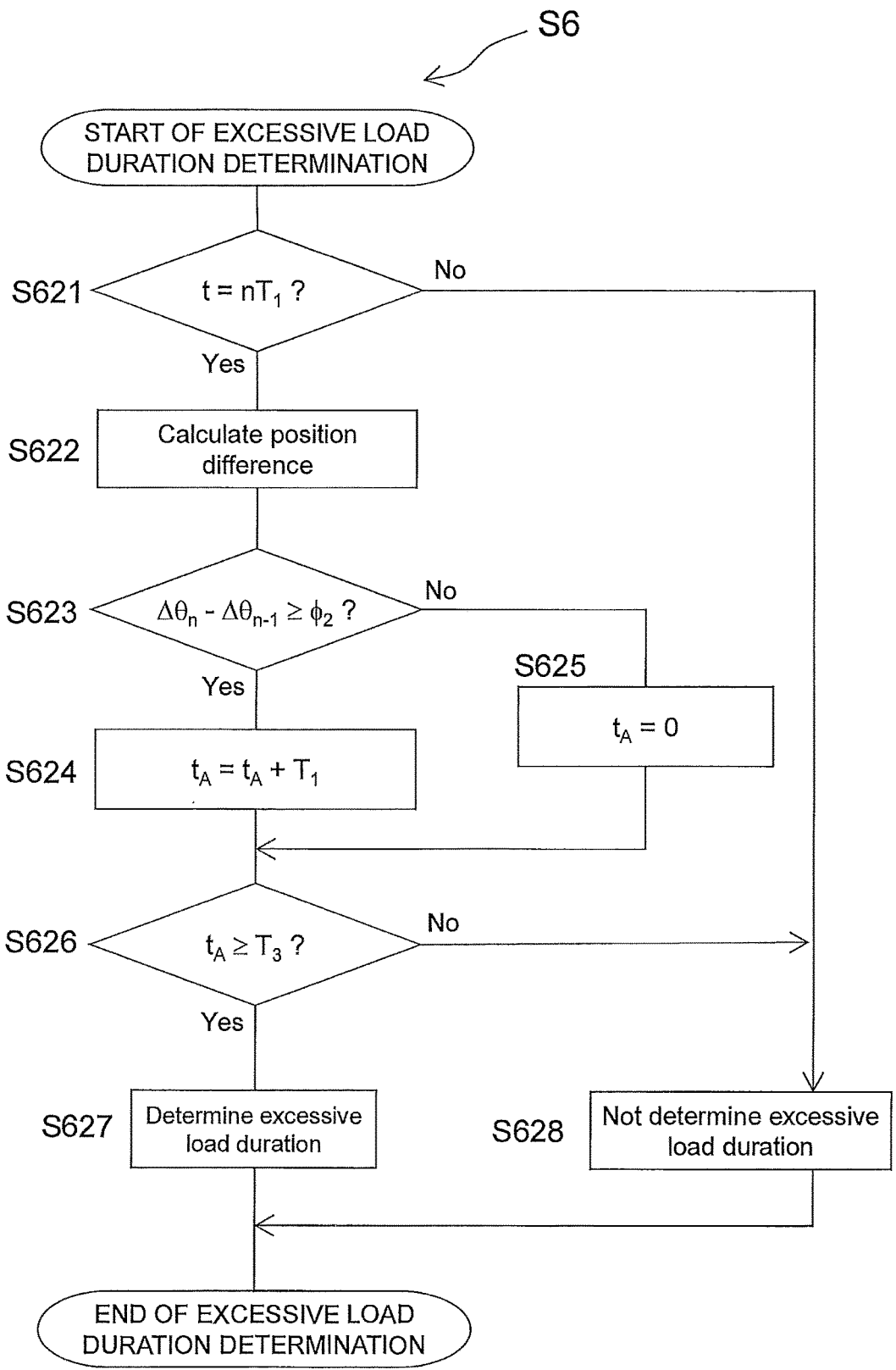
FIG. 17 is a flowchart illustrating an excessive load duration detection method using the position difference.

Next, the excessive load duration detection method using the position difference is described with reference to FIG. 17. FIG. 17 is a flowchart illustrating the excessive load duration detection method using the position difference. In the excessive load duration detection method using the position difference, by determining whether or not a position difference change amount per unit time (first time period $T_1$) is within a predetermined range, it is determined whether or not the excessive load state has continued.

Specifically, the accumulated time measuring unit 1136 first determines whether or not the elapsed time t is a multiple $nT_1$ of the first time period $T_1$ and an integer n (Step S621). If the elapsed time t is a multiple $nT_1$ of the first time period $T_1$ and an integer n ("Yes" in Step S621), the process proceeds to Step S622. On the other hand, if the elapsed time t is not a multiple $nT_1$ of the first time period $T_1$ and an integer n ("No" in Step S621), the accumulated time measuring unit 1136 determines that the excessive load state has not continued (Step S628) and finishes the excessive load duration detection.

If the elapsed time t is a multiple $nT_1$ of the first time period $T_1$ and an integer n ("Yes" in Step S621), the accumulated time measuring unit 1136 instructs the position difference calculation unit 1132 to calculate the position difference $\Delta\theta_n$ when the elapsed time t is $nT_1$ (Step S622). Further, the accumulated time measuring unit 1136 stores the calculated position difference as the accumulated and maintained position difference $\Delta\theta_n$ at the elapsed time $t=nT_1$ in the storage device of the motor control unit 113a or the like.

Next, the accumulated time measuring unit 1136 determines whether or not the position difference generated per the first time period $T_1$ is the second threshold $\varphi_2$ or higher (Step S623). Specifically, the determination is performed as follows. First, the accumulated time measuring unit 1136 reads out the position difference $\Delta\theta_{n-1}$ accumulated and maintained at the elapsed time $t=(n-1)T_1$ that was measured last time, from the storage device of the motor control unit 113a or the like. Further, the accumulated time measuring unit 1136 calculates the difference $\Delta\theta_n - \Delta\theta_{n-1}$ between the position difference $\Delta\theta_n$ at the elapsed time $t=nT_1$ and the position difference $\Delta\theta_{n-1}$ at the elapsed time $t=(n-1)T_1$. In this way, the position difference generated per the first time period $T_1$ (i.e., per unit time) at the elapsed time $t=nT_1$ is calculated. After that, the accumulated time measuring unit 1136 determines whether or not $\Delta\theta_n - \Delta\theta_{n-1}$ is the second threshold $\varphi_2$ or higher.

If $\Delta\theta_n - \Delta\theta_{n-1}$ is the second threshold $\varphi_2$ or higher ("Yes" in Step S623), it is determined to be the excessive load state. Further, the accumulated time measuring unit 1136 adds $T_1$ to the accumulated time $t_A$ so as to make a new accumulated time $t_A$ (Step S624). In this way, the accumulated time measuring unit 1136 can measure the period while the state where $\Delta\theta_n-\Delta\theta_{n-1}$ is the second threshold $\varphi_2$ or higher (i.e., the excessive load state) continues (the accumulated time $t_A$). After the accumulated time $t_A$ is updated, the process proceeds to Step S626.

On the other hand, if $\Delta\theta_n-\Delta\theta_{n-1}$ is lower than the second threshold $\varphi_2$ ("No" in Step S623), the accumulated time measuring unit 1136 determines not to be the excessive load state. Further, the accumulated time measuring unit 1136 resets the accumulated time $t_A$ to zero (Step S625). After the accumulated time $t_A$ is reset, the process proceeds to Step S626.

Further, in Step S623, it is not determined whether or not the difference $\Delta\theta_n-\Delta\theta_{n-1}$ between the position difference $\Delta\theta_n$ at the elapsed time $t=nT_1$ and the position difference $\Delta\theta_{n-1}$ at the elapsed time $t=(n-1)T_1$ is lower than the first threshold $\varphi_1$. It is because that the excessive load duration detection is executed after it is determined in Step S5 of the flowchart illustrated in FIG. 9 that the position difference excessiveness is not generated (i.e., "No" in Step S5). In other words, it is already determined in Step S5 that $\Delta\theta_n-\Delta\theta_{n-1}$ is lower than the first threshold $\varphi_1$.

However, without limiting to this, the accumulated time measuring unit 1136 may determine in Step S623 whether or not $\Delta\theta_n-\Delta\theta_{n-1}$ is lower than the first threshold $\varphi_1$.

In Step S626, the determination unit 1134 determines whether or not the accumulated time $t_A$ is the third time period $T_3$ or longer. If it is determined that the accumulated time $t_A$ is the third time period $T_3$ or longer ("Yes" in Step S626), the determination unit 1134 determines that the excessive load state has continued (Step S627) and finishes the excessive load duration detection.

On the other hand, if it is determined that the accumulated time $t_A$ is shorter than the third time period $T_3$ ("No" in Step S626), the determination unit 1134 determines that the excessive load state has not continued (Step S628) and finishes the excessive load duration detection.

Figure 18:
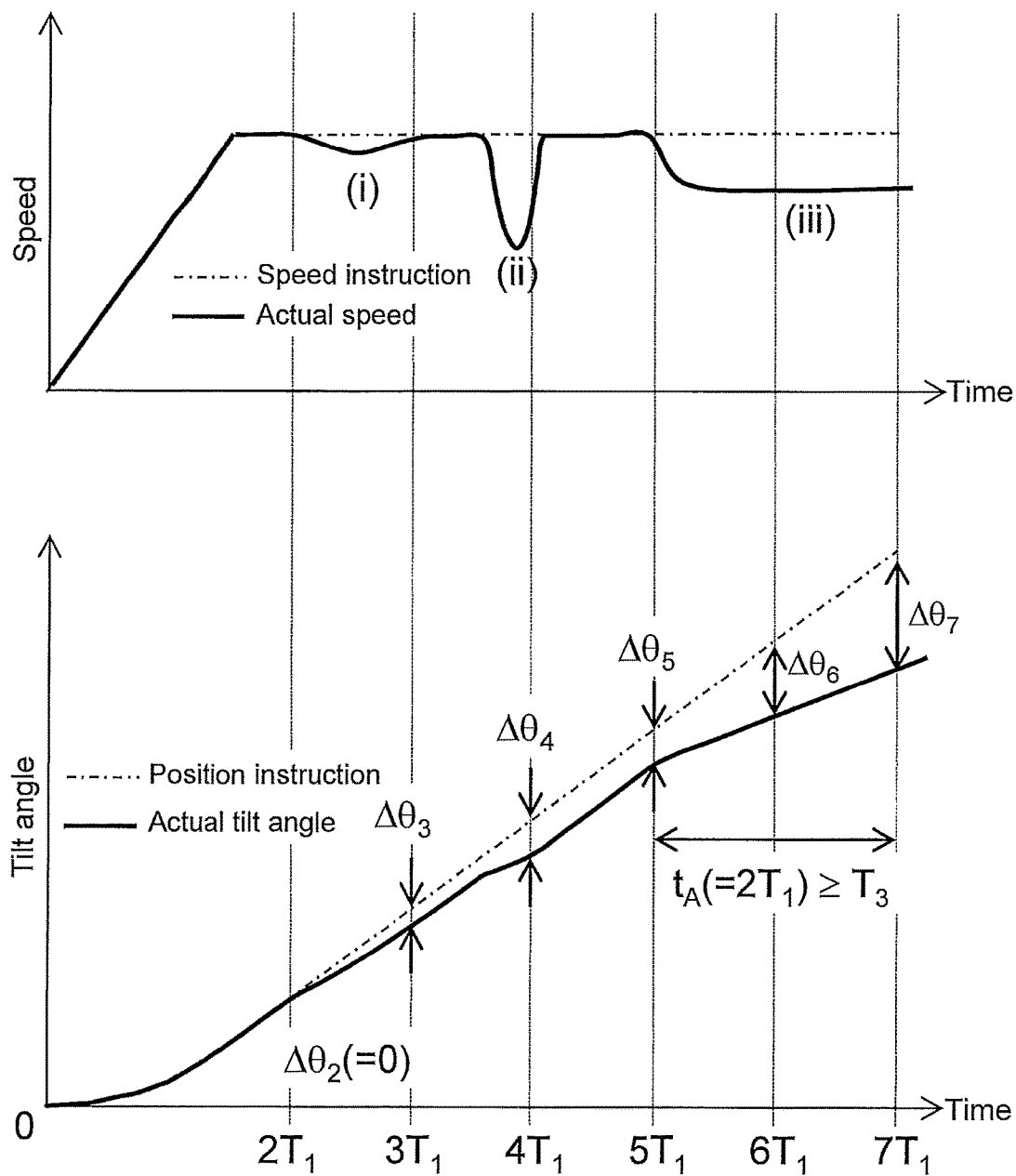
FIG. 18 is a graph illustrating a relationship between an actual tilt angle of the training rod and the instructed tilt angle indicated in the position instruction when the speed change as illustrated in FIG. 15 occurs.

The above-mentioned excessive load duration detection method using the position difference is further described with reference to FIG. 18. FIG. 18 is a graph illustrating a relationship between the actual tilt angle of the training rod 3 and the instructed tilt angle indicated in the position instruction when the speed changes (i) to (iii) as illustrated in FIG. 15 have occurred. In FIG. 18, the speed change (i) occurs between the elapsed time $t=2T_1$ and the elapsed time $t=3T_1$. Further, the position difference $\Delta\theta_2$ at the elapsed time t at $2T_1$ is zero. Accordingly, it means that the position difference $\Delta\theta_3$ per the first time period $T_1$ has occurred when the elapsed time t becomes $3T_1$. However, because the integrated value over time of the speed change (i) (corresponding to $\Delta\theta_3-\Delta\theta_2$) is small, when the elapsed time t becomes $3T_1$, the position difference $\Delta\theta_3-\Delta\theta_2$ generated per the first time period $T_1$ is lower than the second threshold $\varphi_2$. Accordingly, the accumulated time measuring unit 1136 determines not to be the excessive load state at the elapsed time $t=3T_1$.

On the other hand, when the elapsed time t becomes $4T_1$, the position difference $\Delta\theta_4-\Delta\theta_3$ generated per the first time period $T_1$ corresponds to the speed change (ii) and is the second threshold $\varphi_2$ or higher. As a result, the accumulated time $t_A$ is updated to $T_1$. However, when the elapsed time t becomes $5T_1$, the position difference $\Delta\theta_5-\Delta\theta_4$ generated per the first time period $T_1$ is lower than the second threshold $\varphi_2$. It is because the speed change (ii) is generated in a short period. In this case, at the elapsed time $t=5T_1$, the accumulated time $t_A$ is reset to zero. As a result, at the elapsed time $t=5T_1$, the determination unit 1134 determines that the excessive load state has not continued.

Further, after the elapsed time $t=5T_1$, the speed change (iii) is generated. In this case, at the elapsed time $t=6T_1$, the position difference $\Delta\theta_6-\Delta\theta_5$ generated per the first time period $T_1$ is the second threshold $\varphi_2$ or higher. As a result, the accumulated time $t_A$ is updated to $T_1$. In addition, also at the elapsed time $t=7T_1$, the position difference $\Delta\theta_7-\Delta\theta_6$ generated per the first time period $T_1$ has substantially the same value as the position difference $\Delta\theta_6-\Delta\theta_5$ generated per the first time period $T_1$ at the elapsed time $t=6T_1$, and is the second threshold $\varphi_2$ or higher. As a result, at the elapsed time $t=7T_1$, $T_1$ is added to the accumulated time $t_A$ so that the accumulated time $t_A$ is updated to $2T_1$.

Here, if the accumulated time $t_A$ is the third time period $T_3$ or longer, the determination unit 1134 determines that the excessive load state has continued.

From the comparison between FIG. 15 and FIG. 18 described above, it can be said that the changes (1) to (3) of the feedback current I generated due to the speed changes (i) to (iii) correspond well to the position difference change amount generated per unit time (the first time period $T_1$). In other words, if the change of the feedback current I illustrated in FIG. 15 is (1) or (2) in FIG. 15, a change amount of the position difference generated per the first time period $T_1$ is also small. On the other hand, if the current value of the feedback current I as (3) illustrated in FIG. 15 continues to increase, the position difference continued to increase.

This indicates that the change of the feedback current I can also be predicted from the position difference change amount generated per unit time. In other words, the change of the load applied on the limb by the training rod 3 during the training, which is generated due to the change of the feedback current I, can be detected from the position difference change amount generated per unit time.

In this way, the accumulated time measuring unit 1136 measures the period while the position difference generated per unit time (the first time period $T_1$) is the second threshold $\varphi_2$ or higher (and lower than the first threshold $\varphi_1$), and hence the period while the slow position difference change continues (the accumulated time $t_A$) can be measured. At the same time, the change of the load applied on the limb, which is generated due to a speed change as the speed changes (i) to (iii), can also be monitored. Further, by measuring the period while the slow position difference change continues (the accumulated time $t_A$), it is possible to determine whether or not the state where an excessive load is applied on the limb (the excessive load state) has occurred continuously.

Further, when detecting the excessive load duration, as illustrated in FIGS. 7B and 7C, the motor control unit 113*a* (113*b* or 113*c*) including both the feedback current detection unit 1133 and the accumulated time measuring unit 1136 may be capable of selecting whether to detect the excessive load duration on the basis of the feedback current I or to detect the excessive load duration on the basis of the position difference.

In this way, if the feedback current I cannot be detected due to a malfunction of the feedback current detection unit 1133, or if the position difference cannot be calculated due to a malfunction of the accumulated time measuring unit 1136 (the tilt angle calculation unit 1131, the position difference calculation unit 1132, or the first rotation information detection sensor 135*a*-1), it is possible to determine whether or not the excessive load state has occurred continuously on the basis of the other measured amount that can be normally detected or calculated.

In addition, the second threshold $\varphi_2$ is a threshold for determining that an excessive load is not applied on the limb of the patient. The excessive load duration determination can be appropriately used in a case where it is necessary to determine an error in such a case where (1) a difficulty level of the set training program is too high for the patient to appropriately carry out the training program, and/or (2) a life span of a component of the training apparatus 100 is approaching and there is a sign that the component will be broken down soon.

As a result, on the basis of the excessive load duration determination, the patient can carry out the appropriate training program in accordance with the symptoms.

(6) Effects of this Embodiment

Hereinafter, effects of this embodiment are described.

The training apparatus 100 (an example of the training apparatus) is a training apparatus for training an upper limb and/or a lower limb of a patient (an example of the patient) in accordance with a training program (an example of the training program). The training apparatus 100 includes the fixed frame 1 (an example of the fixed frame), the training rod 3 (an example of the training rod), the X-axis direction tilt motor 135b (an example of the motor), the Y-axis direction tilt motor 135a (an example of the motor), the first rotation information detection sensor 135a-1 (an example of the rotation information detection sensor), the second rotation information detection sensor 135b-1 (an example of the rotation information detection sensor), the tilt angle calculation unit 1131 (an example of the tilt angle calculation), the feedback current detection unit 1133 (an example of the feedback current detection unit), the position difference calculation unit 1132 (an example of the position difference calculation unit), and the determination unit 1134 (an example of the determination unit). The fixed frame 1 is placed on or in the vicinity of a floor. The training rod 3 is supported by the fixed frame 1 in a manner capable of tilting about at least the X-axis or the Y-axis (an example of the predetermined tilting axis). Further, the training rod 3 holds the limb. The X-axis direction tilt motor 135b and the Y-axis direction tilt motor 135a tilt the training rod 3 about the X-axis and the Y-axis, respectively. The first rotation information detection sensor 135a-1 and the second rotation information detection sensor 135b-1 output an amount of rotation of the Y-axis direction tilt motor 135a and an amount of rotation of the X-axis direction tilt motor 135b, respectively. The tilt angle calculation unit 1131 calculates a tilt angle of the training rod 3 (an example of the tilt angle) on the basis of the amount of rotation of the X-axis direction tilt motor 135b and the amount of rotation of the Y-axis direction tilt motor 135a. The feedback current detection unit 1133 detects current values of the feedback currents I (an example of the feedback current values) of the X-axis direction tilt motor 135b and the Y-axis direction tilt motor 135a. The position difference calculation unit 1132 calculates a position difference (an example of the position difference) every time when the first time period $T_1$ (an example of the first time period) elapses. Here, the position difference is a difference between an actual tilt angle of the training rod 3 and the instructed tilt angle that is an tilt angle of the training rod 3 instructed by the training program (an example of the instructed tilt angle). The determination unit 1134 determines an error if the position difference generated in the first time period $T_1$ is the first threshold $\varphi_1$ (an example of the first threshold) or higher, or if the current value of the feedback current I keeps the first current value $I_1$ (an example of the first current value) or higher for the second time period $T_2$ (an example of the second time period) or longer.

In the training apparatus 100, when the X-axis direction tilt motor 135b and the Y-axis direction tilt motor 135a control the training rod 3, the position difference calculation unit 1132 calculates the position difference every first time period $T_1$. Further, when the position difference generated in the first time period $T_1$ becomes the first threshold $\varphi_1$ or higher, the determination unit 1134 determines that there is a malfunction in the training apparatus 100 or that the position difference has rapidly changed in a short period, so as to determine an error.

On the other hand, when the X-axis direction tilt motor 135b and the Y-axis direction tilt motor 135a control the training rod 3 in the same manner, the feedback current detection unit 1133 monitors current values of the feedback currents I supplied to the X-axis direction tilt motor 135b and the Y-axis direction tilt motor 135a. Further, if the state where the current value of the feedback current I is the first current value $I_1$ or higher has continued for the second time period $T_2$ or longer, the determination unit 1134 similarly determines that there is a malfunction in the training apparatus 100 or that a slow position difference change has continued for a long period so as to determine an error.

In this way, the training apparatus 100 monitors a change amount of the position difference per the first time period $T_1$. Accordingly, the determination unit 1134 can determine that the position difference has rapidly changed in a short period with reference to the first time period $T_1$ if the change amount of the position difference per the first time period $T_1$ is large. Further, if a rapid position difference change in a short period has occurred, the determination unit 1134 can determine an error.

In addition, the training apparatus 100 monitors the current values of the feedback currents I input to the X-axis direction tilt motor 135b and the Y-axis direction tilt motor 135a so as to monitor torques necessary for the X-axis direction tilt motor 135b and the Y-axis direction tilt motor 135a to tilt the training rod 3.

Further, the training apparatus 100 controls the training rod 3 to be at the tilt angle instructed by the training program, and hence the current value of the feedback current I changes in accordance with a level of the position difference change. Accordingly, it is possible to monitor whether a slow position difference change has occurred or a rapid position difference change has occurred, on the basis of the current value of the feedback current I and the predetermined determination time period.

In addition, the determination unit 1134 determines an error when the state where the current value of the feedback current I is the first current value $I_1$ or higher continues for the second time period $T_2$ or longer. In this way, in the determination time period, if the position difference is within a constant range, i.e., if the training rod 3 (the X-axis direction tilt motor 135b and the Y-axis direction tilt motor 135a) does not apply an excessive load on the limb of the patient, or if the position difference slowly changes (if the limb of the patient follows the movement of the training rod 3 to a certain extent so that the training can be continued), the determination unit 1134 can control the training rod 3 so that the training is continued until the second time period $T_2$.

The training rod 3 is expandable and contractible in the longitudinal axis direction (an example of the longitudinal axis direction). Because the training rod 3 is expandable and contractible in the longitudinal axis direction, the training of the upper limb or the lower limb in the longitudinal direction of the training rod 3 can be also carried out.

The training apparatus 100 further includes the training instruction unit 5 (an example of the information providing unit). The training instruction unit 5 provides the user with visual or auditory information when the determination unit 1134 determines an error.

In this way, the patient and the user of the training apparatus 100 can be notified about a status of the training apparatus 100, i.e., that an error has occurred in the training apparatus 100 and/or about a cause of the error.

When the patient has moved the training rod 3 to reach the target tilt angle (an example of the preset passing point in the training route set by the training program), the training instruction unit 5 provides the user with visual information and/or auditory information. In this way, the user can know that the training rod 3 has been operated just in accordance with the training program. In addition, because the patient is provided with the visual or auditory information when the patient has moved the training rod 3 to reach the preset passing point, the patient can maintain a motivation to continue the training.

The training apparatus 100 further includes the feedback current limiting unit 1137 (an example of the feedback current limiting unit). When the determination unit 1134 determines an error, the feedback current limiting unit 1137 limits the current values of the feedback currents I of the X-axis direction tilt motor 135b and the Y-axis direction tilt motor 135a to the appropriately preset second current value $I_2$ (an example of the second current value).

In this way, when an error has occurred in the training apparatus 100, torques output from the X-axis direction tilt motor 135b and the Y-axis direction tilt motor 135a can be limited. As a result, the training rod 3 can be controlled for carrying out the rehabilitation without applying an excessive load on the patient during the training.

The second current value $I_2$ is a current value $a \times I_R$ (an example of the current value) as an multiple of the rated current $I_R$ (an example of the rated current) of capable being supplied to the X-axis direction tilt motor 135b and the Y-axis direction tilt motor 135a and a predetermined number "a" smaller than one (an example of the predetermined). In this way, the rated current $I_R$ is not supplied to the X-axis direction tilt motor 135b and the Y-axis direction tilt motor 135a for a long period. As a result, the training rod 3 can be controlled without applying an excessive load on the patient.

In addition, an excessive electric load can be avoided from being applied on the control unit 11 of the training apparatus 100.

The training apparatus 100 further includes the accumulated time measuring unit 1136. The accumulated time measuring unit 1136 measures the accumulated time $t_A$ (an example of the accumulated time) in which the position difference generated in the first time period $T_1$ is the second threshold $\varphi_2$ (an example of the second threshold) or higher and is lower than the first threshold $\varphi_1$. Here, the second threshold $\varphi_2$ is lower than the first threshold $\varphi_1$. In this case, the determination unit 1134 determines an error when the accumulated time $t_A$ is the third time period $T_3$ (an example of the third time period) or longer.

Because the accumulated time measuring unit 1136 measures the time in which the position difference generated in the first time period $T_1$ is the second threshold $\varphi_2$ or higher and lower than the first threshold $\varphi_1$, the period while the slow position difference change continues (the accumulated time $t_A$) can be measured. In addition, because the determination unit 1134 determines an error if the accumulated time $t_A$ is the third time period $T_3$ or longer, the training can be continued for the third time period $T_3$ with respect to the slow position difference change.

The second threshold $\varphi_2$ is a threshold for determining that an excessive load is not applied on the limb of the patient, and hence an error generated in this case can be appropriately used for detecting a case where the difficulty level of the set training program is too high for the patient to appropriately carry out the training program or a case where there is a sign that a component of the apparatus is gradually broken. On the basis of this determination, the patient can carry out an appropriate training program in accordance with the symptoms.

The training apparatus 100 further includes the instruction generation unit 111 (an example of the instruction generation unit) and the motor drive unit 1135 (an example of the motor drive unit). The instruction generation unit 111 generates the speed instruction (an example of the speed instruction), which is an instruction for controlling the rotation speeds (an example of the speeds) of the X-axis direction tilt motor 135b and the Y-axis direction tilt motor 135a, in accordance with the training program. The motor drive unit 1135 drives the X-axis direction tilt motor 135b and the Y-axis direction tilt motor 135a on the basis of the speed instruction. In addition, the speed instruction includes at least an acceleration instruction (an example of the acceleration instruction) for accelerating the X-axis direction tilt motor 135b and the Y-axis direction tilt motor 135a and a deceleration instruction (an example of the deceleration instruction) for decelerating the X-axis direction tilt motor 135b and the Y-axis direction tilt motor 135a. Further, the motor drive unit 1135 drives the X-axis direction tilt motor 135b and the Y-axis direction tilt motor 135a so as to accumulate and maintain the position difference when the acceleration instruction is executed. Using the speed instruction generated by the instruction generation unit 111, which includes at least the acceleration instruction and the deceleration instruction, the X-axis direction tilt motor 135b and the Y-axis direction tilt motor 135a are driven, and hence the X-axis direction tilt motor 135b and the Y-axis direction tilt motor 135a can be smoothly operated in accordance with the training program and a patient's operation. As a result, the patient can operate the training rod 3 as intended.

In addition, the motor drive unit 1135 drives the X-axis direction tilt motor 135b and the Y-axis direction tilt motor 135a so that the position difference is accumulated and maintained when the acceleration instruction is executed, and hence the patient can continue the training using the training apparatus 100 even if the position difference occurs when the patient starts or stops the training rod 3 in particular when the acceleration instruction is executed, which is apt to cause the position difference in a short period. In addition, because the position difference is accumulated and maintained, a state of the limb of the patient during the training can be grasped on the basis of the accumulated and maintained amount of the position difference.

The speed instruction further includes the constant speed instruction (an example of the constant speed instruction). The constant speed instruction is an instruction for rotating the X-axis direction tilt motor 135b and the Y-axis direction tilt motor 135a at a constant rotation speed. In addition, the constant speed instruction is disposed before or after the acceleration instruction or the deceleration instruction. In addition, the motor drive unit 1135 drives the X-axis direction tilt motor 135b and the Y-axis direction tilt motor 135a so that the position difference is accumulated and maintained when the constant speed instruction is executed.

Because the speed instruction further includes the constant speed instruction, the X-axis direction tilt motor 135b and the Y-axis direction tilt motor 135a can be smoothly operated at a constant speed on the basis of the feedback current value even if the training rod 3 is operated at a large tilt angle. In addition, because the X-axis direction tilt motor 135b and the Y-axis direction tilt motor 135a are driven so that the position difference is accumulated and maintained when the constant speed instruction is executed, the patient can continue the training using the training apparatus 100 even if a relatively large torque is required and hence the position difference is apt to occur, for example, even if the training rod 3 is operated at a large tilt angle.

When the acceleration instruction and/or the constant speed instruction is executed, the motor drive unit 1135 drives the X-axis direction tilt motor 135b and the Y-axis direction tilt motor 135a so as to follow only the speed instruction. In this way, when the acceleration instruction is executed and/or when the constant speed instruction is executed, the X-axis direction tilt motor 135b and the Y-axis direction tilt motor 135a can be driven regardless of the position difference. As a result, even if a relatively large motor torque is required, and hence a position difference is apt to occur, for example, even if the training rod 3 is operated at a large tilt angle, the patient can continue the training using the training apparatus 100.

The instruction generation unit 111 further generates the position instruction (an example of the position instruction) for controlling the tilt angle of the training rod 3 in accordance with the training program. In addition, when the deceleration instruction is executed, the motor drive unit 1135 drives the X-axis direction tilt motor 135b and the Y-axis direction tilt motor 135a so as to follow the speed instruction and the position instruction.

In this way, the motor drive unit 1135 can control the X-axis direction tilt motor 135b and the Y-axis direction tilt motor 135a so that the training rod 3 can reach the target tilt angle instructed by the training program with a difference as small as possible. As a result, when the position information of the training rod 3 is fed back as visual information to the patient, this position information can be appropriately used.

When the tilt angle reaches the instructed tilt angle $\theta_d$ (an example of the deceleration start position), the motor drive unit 1135 resets the accumulated and maintained position difference. In this way, when the speed is decreased, it is possible to prevent excessive increases of the rotation speeds of the X-axis direction tilt motor 135b and the Y-axis direction tilt motor 135a due to temporary increase of the position difference and correction of the position difference. As a result, the patient can continue the training.

2. Other Embodiments

Although an embodiment of the present invention is described above, the present invention is not limited to the embodiment but can be modified variously within the scope of the spirit of the invention. In particular, a plurality of embodiments and variations described in this specification can be arbitrarily combined as necessary.

(A) Another Embodiment Concerning Motor Control

In the first embodiment described above, only when the deceleration instruction of the speed instruction is executed, the Y-axis direction tilt motor 135a (the X-axis direction tilt motor 135b or the expansion/contraction motor 359) is controlled so that the tilt angle of the training rod 3 follows the instructed tilt angle instructed by the position instruction (position control). However, this is not a limitation. Also when the acceleration instruction of the speed instruction is executed and/or when the constant speed instruction is executed, the Y-axis direction tilt motor 135a (the X-axis direction tilt motor 135b or the expansion/contraction motor 359) may be controlled by the position control and the speed control. In this case, the switching unit 1135-8 of the motor drive unit 1135 is not necessary in particular.

When the acceleration instruction of the speed instruction is executed and/or when the constant speed instruction is executed, if the Y-axis direction tilt motor 135a (the X-axis direction tilt motor 135b or the expansion/contraction motor 359) is controlled by the position control, it is preferred to adjust the control gains $K_{pp}$ and $K_{ip}$ or to adjust the weighting value of the second control amount of the combining unit 1135-7 so that the tilt angle speed of the training rod 3 does not become excessively large.

In this way, the tilt angle of the training rod 3 can follow the instructed tilt angle without excessively increasing the tilt angle speed of the training rod 3.

(B) Another Embodiment when Error Occurs

In the first embodiment described above, when the determination unit 1134 determines an error, the feedback current I supplied to the Y-axis direction tilt motor 135a (the X-axis direction tilt motor 135b or the expansion/contraction motor 359) is limited to the second current value $I_2$. However, this is not a limitation. When the determination unit 1134 determines an error, it is possible to stop the control (rotation) of the Y-axis direction tilt motor 135a (the X-axis direction tilt motor 135b or the expansion/contraction motor 359). Alternatively, it is possible to stop the training program.

In this way, when the determination unit 1134 determines an error, it is possible to securely stop the training apparatus 100.

INDUSTRIAL APPLICABILITY

The present invention can be widely applied to a training apparatus including a training rod driven by a motor, for carrying out training of a limb of a patient in accordance with a predetermined training program.

REFERENCE SIGNS LIST 100 training apparatus
1 fixed frame
11 control unit
111 instruction generation unit
113a, 113b, 113c motor control unit
1131 tilt angle calculation unit
1132 position difference calculation unit
1133 feedback current detection unit
1134 determination unit
1135 motor drive unit
1135-1 speed control unit
1135-2 position control unit
1135-3 speed calculation unit
1135-4 power supply unit
1135-5 current limiting unit
1135-6a first difference calculation unit
1135-6b second difference calculation unit
1135-7 combining unit
1135-8 switching unit
1135-9 position difference setting unit
1136 accumulated time measuring unit
1137 feedback current limiting unit
13 training rod tilt mechanism
131 X-axis direction tilt member 131a, 131b shaft
133 Y-axis direction tilt member
133a, 133b shaft
135a Y-axis direction tilt motor
135a-1 first rotation information detection sensor
135b X-axis direction tilt motor
135b-1 second rotation information detection sensor
15a, 15b training rod tilt mechanism fixing member
3 training rod
31 limb support member
33 fixed stay
35 expansion/contraction mechanism
351 movable stay
353 cover
355 nut
357 threaded shaft
359 expansion/contraction motor
359-1 third rotation information detection sensor
37 guide rail
5 training instruction unit
7 fixing member
9 chair
91 chair connecting member
I feedback current
$I_1$ first current value
$I_2$ second current value
$I_{max}$ maximum current
$I_R$ rated current
$K_{pv}$, $K_{iv}$ control gain in speed control
$K_{pp}$, $K_{pv}$ control gain in position control
S, S' space
$T_1$ first time period
$T_2$ second time period
$T_3$ third time period
n integer
t, $t_1$, $t_2$, $t_3$, $t_4$, $t_5$, $t_{dc}$, $t_{da}$, $t_a$, $t_b$ elapsed time
$t_A$ accumulated time
$\Delta v$ speed difference
$\theta_d$ (instructed) tilt angle corresponding to deceleration start position
$\Delta\theta_{da}$, $\Delta\theta_A$, $\Delta\theta_B$, $\Delta\theta_n$, $\Delta\theta_{n-1}$, $\Delta\theta_2$, $\Delta\theta_3$, $\Delta\theta_4$, $\Delta\theta_5$, $\Delta\theta_6$, $\Delta\theta_7$ position difference
$\varphi_1$ first threshold
$\varphi_2$ second threshold

The invention claimed is:
1. A training apparatus for training upper and/or lower limbs of a user in accordance with a predetermined training program, the training apparatus comprising:
a fixed frame placed on or in the vicinity of a floor;
a training rod supported by the fixed frame in a manner capable of tilting about a predetermined tilting axis with at least one degree of freedom to hold a limb;
a motor configured to tilt the training rod about the tilting axis;
a rotation information detection sensor configured to output an amount of rotation of the motor;
a tilt angle calculating unit configured to calculate a tilt angle of the training rod on the basis of the amount of rotation of the motor;
a position difference calculating unit configured to calculate a position difference every time when a predetermined first time period elapses, the position difference being a difference between an actual tilt angle of the training rod and an instructed tilt angle of the training rod instructed by the training program; and
a determination unit configured to determine an error when a change of the position difference per the first time period is a predetermined first threshold or higher.
2. The training apparatus according to claim 1, wherein the training rod is capable of expanding and contracting in a longitudinal axis direction.
3. The training apparatus according to claim 1, further comprising an information providing unit configured to provide the user with visual or auditory information when the determination unit determines an error.
4. The training apparatus according to claim 3, wherein the information providing unit provides the user with the visual or auditory information when the user has moved the training rod to reach a preset passing point in a training route set by the training program.
5. The training apparatus according to claim 1, wherein rotation of the motor is stopped when the determination unit determines an error.
6. The training apparatus according to claim 1, further comprising a feedback current limiting unit configured to limit the feedback current of the motor to a predetermined second current value or lower when the determination unit determines an error.
7. The training apparatus according to claim 1, further comprising:
an instruction generation unit configured to generate a speed instruction for controlling a speed of the motor in accordance with the training program; and
a motor drive unit configured to drive the motor in accordance with the speed instruction; wherein
the speed instruction includes at least one of an acceleration instruction for accelerating the motor and an deceleration instruction for decelerating the motor, and
the motor drive unit drives the motor so that the position difference is accumulated and maintained when the acceleration instruction is executed.
8. The training apparatus according to claim 7, wherein the speed instruction further includes a constant speed instruction for rotating the motor at a constant speed before or after the acceleration instruction or the deceleration instruction, and
the motor drive unit drives the motor so that the position difference is accumulated and maintained when the constant speed instruction is executed.
9. The training apparatus according to claim 7, wherein the motor drive unit drives the motor so as to follow only the speed instruction when the acceleration instruction and/or the constant speed instruction is executed.
10. The training apparatus according to claim 7, wherein the instruction generation unit further generates a position instruction for controlling the tilt angle of the training rod in accordance with the training program, and
the motor drive unit drives the motor so as to follow the speed instruction and the position instruction when the deceleration instruction is executed.
11. The training apparatus according to claim 7, wherein the accumulated position difference is reset when the tilt angle of the training rod reaches a deceleration start position.
12. The training apparatus according to claim 1, further comprising a feedback current detection unit configured to detect a feedback current of the motor,
wherein the determination unit is configured to determine the error when the feedback current is kept at a first current value or higher for a predetermined second time period or longer.

13. A training apparatus for training upper and/or lower limbs of a user in accordance with a predetermined training program, the training apparatus comprising:
- a fixed frame placed on or in the vicinity of a floor;
- a training rod supported by the fixed frame in a manner capable of tilting about a predetermined tilting axis with at least one degree of freedom, so as to hold a limb;
- a motor configured to tilt the training rod about the tilting axis;
- a rotation information detection sensor configured to output an amount of rotation of the motor;
- a tilt angle calculating unit configured to calculate a tilt angle of the training rod on the basis of the amount of rotation of the motor;
- a feedback current detection unit configured to detect a feedback current of the motor;
- a position difference calculation unit configured to calculate a position difference every time when a predetermined first time period elapses, the position difference being a difference between an actual tilt angle of the training rod and an instructed tilt angle of the training rod instructed by the training program;
- a determination unit configured to determine an error when the position difference during the first time period is a predetermined first threshold or higher, or when the feedback current is kept at a first current value or higher for a predetermined second time period or longer; and
- a feedback current limiting unit configured to limit the feedback current of the motor to a predetermined second current value or lower when the determination unit determines an error,
- wherein the second current value is calculated by multiplying a rated current of the motor by a predetermined number smaller than one.

14. A training apparatus for training upper and/or lower limbs of a user in accordance with a predetermined training program, the training apparatus comprising:
- a fixed frame placed on or in the vicinity of a floor;
- a training rod supported by the fixed frame in a manner capable of tilting about a predetermined tilting axis with at least one degree of freedom, so as to hold a limb;
- a motor configured to tilt the training rod about the tilting axis;
- a rotation information detection sensor configured to output an amount of rotation of the motor;
- a tilt angle calculating unit configured to calculate a tilt angle of the training rod on the basis of the amount of rotation of the motor;
- a feedback current detection unit configured to detect a feedback current of the motor;
- a position difference calculation unit configured to calculate a position difference every time when a predetermined first time period elapses, the position difference being a difference between an actual tilt angle of the training rod and an instructed tilt angle of the training rod instructed by the training program;
- a determination unit configured to determine an error when the position difference during the first time period is a predetermined first threshold or higher, or when the feedback current is kept at a first current value or higher for a predetermined second time period or longer; and
- an accumulated time measuring unit configured to measure an accumulated time when the position difference during the first time period is a second threshold or higher and lower than the first threshold, the second threshold being less than the first household,
- wherein the determination unit determines the error when the accumulated time is a predetermined third time period or longer.

* * * * *